US008247214B2

(12) United States Patent
Sowerby et al.

(10) Patent No.: US 8,247,214 B2
(45) Date of Patent: Aug. 21, 2012

(54) DETECTING, MEASURING AND CONTROLLING PARTICLES AND ELECTROMAGNETIC RADIATION

(75) Inventors: Stephen John Sowerby, Dunedin (NZ); George Bouet Petersen, Dunedin (NZ); Murray Frederick Broom, Dunedin (NZ); Martin David Jones, Port Chalmers (NZ)

(73) Assignee: Izon Science Limited, Dunedin (NZ)

( * ) Notice: Subject to any disclaimer, the term of this patent is extended or adjusted under 35 U.S.C. 154(b) by 655 days.

(21) Appl. No.: 11/721,047

(22) PCT Filed: Jul. 13, 2005

(86) PCT No.: PCT/EP2005/053366
§ 371 (c)(1),
(2), (4) Date: Jun. 7, 2007

(87) PCT Pub. No.: WO2006/063872
PCT Pub. Date: Jun. 22, 2006

(65) Prior Publication Data
US 2010/0021883 A1 Jan. 28, 2010

(30) Foreign Application Priority Data
Dec. 13, 2004 (NZ) ........................ 537147

(51) Int. Cl.
*C12Q 1/68* (2006.01)
*C12M 1/36* (2006.01)
*G01N 27/00* (2006.01)
*B01D 63/00* (2006.01)
(52) U.S. Cl. ............... 435/283.1; 435/6.1; 435/287.2; 210/321.6; 210/321.84; 324/71.4
(58) Field of Classification Search ............... None
See application file for complete search history.

(56) References Cited

U.S. PATENT DOCUMENTS
3,395,344 A 7/1968 Bader
(Continued)

FOREIGN PATENT DOCUMENTS
EP 0 614 077 A2 9/1994
(Continued)

OTHER PUBLICATIONS
International Search Report for corresponding Application No. PCT/EP2005/053366 mailed Dec. 20, 2005.
(Continued)

*Primary Examiner* — Betty Forman
(74) *Attorney, Agent, or Firm* — Renner, Otto, Boisselle & Sklar, LLP

(57) ABSTRACT

A method is provided for detecting, measuring or controlling particles and/or electromagnetic radiation, comprising providing a deformable material containing a deformable aperture defining a path for particles or radiation, adjusting the deformable aperture to a prescribed geometry and/or size by deforming the deformable material to change at least one of the parameters of the path defined by the deformable aperture, and causing the particle or radiation to be detected, measured or controlled to enter the deformable aperture. The method includes the step of monitoring the geometry and/or size of the deformable aperture and controlling the adjustment of the size of the deformable aperture in response to such monitoring. The required apparatus is easily fabricated from inexpensive materials. Furthermore the deformable aperture can be tuned to the appropriate geometry post fabrication, and the ability to adjust the aperture geometry renders it capable of discriminating a plurality of differently sized particles.

18 Claims, 13 Drawing Sheets

U.S. PATENT DOCUMENTS

| | | |
|---|---|---|
| 4,684,206 A | 8/1987 | Bednorz et al. |
| 4,832,997 A | 5/1989 | Balanzat et al. |
| 2003/0008308 A1* | 1/2003 | Enzelberger et al. ............ 435/6 |
| 2003/0080042 A1 | 5/2003 | Barth et al. |
| 2003/0098069 A1* | 5/2003 | Sund et al. ................ 137/487.5 |
| 2003/0104428 A1* | 6/2003 | Branton et al. .................. 435/6 |
| 2004/0126531 A1 | 7/2004 | Harvey et al. |
| 2004/0173506 A1* | 9/2004 | Doktycz et al. ................ 210/85 |

FOREIGN PATENT DOCUMENTS

| | | |
|---|---|---|
| EP | 1 211 694 | 6/2002 |
| GB | 2208611 | 4/1989 |
| GB | 2337597 | 11/1999 |
| JP | 1-118747 A | 5/1989 |
| JP | 2003-161691 A | 6/2003 |

OTHER PUBLICATIONS

Li et al.; "Ion-beam sculpting at nanometer length scales"; Nature; vol. 412, Jul. 12, 2001; pp. 166-169; XP002357329.

Translation of Japanese Office Action issued in corresponding Application No. 2007-545990, mailed Jan. 4, 2011.

* cited by examiner

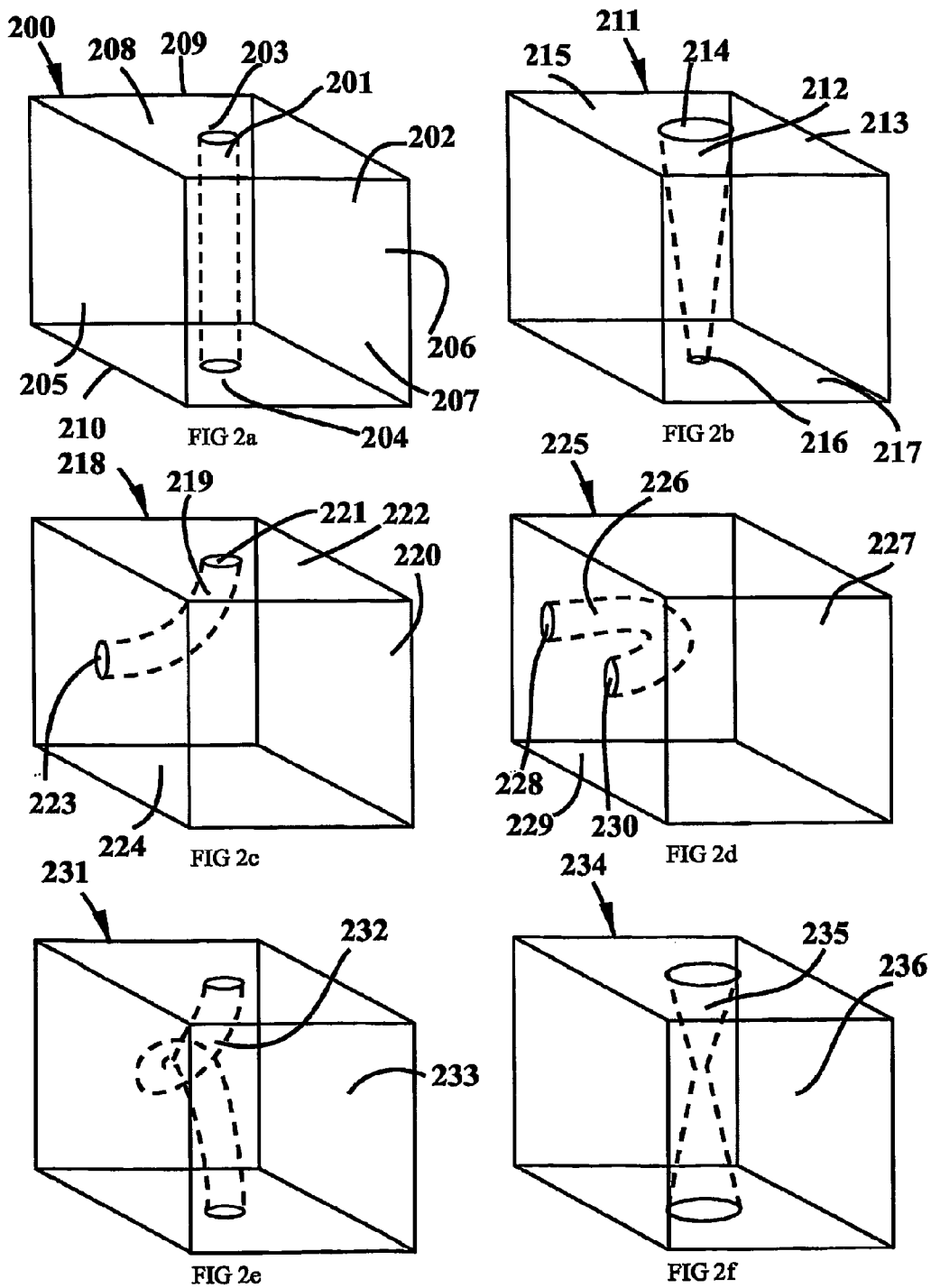

DETECTING, MEASURING AND CONTROLLING PARTICLES AND ELECTROMAGNETIC RADIATION

This invention relates generally to particle-sensitive or radiation-sensitive devices incorporating deformable materials containing deformable apertures, and methods of detecting, measuring or controlling particles and/or electromagnetic radiation and methods for the fabrication of such deformable apertures.

BACKGROUND TO THE INVENTION

A simple way of detecting or measuring particles is with the human sense of vision. However, the resolution of the human eye is limited and particles below approximately 0.05 millimetres in diameter become invisible. Microscopy instruments incorporating optical lenses can achieve a lateral resolution of about 200 nanometres. The physical properties of light limit resolution to about half the wavelength of the light used. Microscopy instruments that employ focused electrons can be used to resolve smaller particles and so extend the imaging range, further allowing for molecular-scale particles and even atoms to be detected or measured.

At the level of microbes, cells of blood, cells of other tissues or microscopic particles of organic or inorganic origin, optical instruments can be used, but the counting of such particles by microscopy has limitations and disadvantages and requires other methods. For example, the preferred method to determine microbe numbers uses a series of dilutions of the sample in question, spreading each dilution on solid microbe culture medium, incubating the culturing media and then counting the number of colonies formed by appropriately diluted samples.

The process of culturing samples amplifies single microbes from invisible cells to colonies that are detectable by the unaided human eye, but such a process has disadvantages and limitations. For example, the large numbers of vessels and materials used for culturing the microbe samples must be sterile and so must either be autoclaved for re-use, or disposed of and replaced. Other disadvantages include the time delay required to culture the microbes to sufficient numbers to be detected, the space and energy requirements to culture the microbes, and the fact that, for disease-causing pathogenic microbes, culturing of samples requires specially constructed containment facilities.

Detection and analysis of the biochemical components of life has utility in the fields of molecular biology, biochemistry, biotechnology, genetics, medicine and nanometre-scale technologies. Electron microscopy methods can be applied to the detection and analysis of molecular particles. However, electron microscopy of molecular particles suffers from the fact that high vacuum conditions are required for the microscopy method, necessitating dehydration of the sample and specialized sample preparation methods, the fact that biological particles lack sufficient contrast in the electron beam and so require a metal coating which obscures the fine detail of the particles and the fact that the high energy of the focused electron beams can shift atoms and damage surfaces.

Methods for detecting and analyzing molecular particles depend on separation methods, most typically centrifugation, electrophoresis or chromatography (See Alberts et al (1994) "*Molecular Biology of the Cell*", Garland publishing, Inc., NY.). Detection methods most typically must also be applied to populations of molecules and require the use of sophisticated high-resolution optical instruments.

Many technological processes benefit from detecting and analyzing molecular particles. For example, the determination of the nucleotide sequence of nucleic acid macromolecules is most typically achieved on short (100-800) nucleotide fragments by generating families of related molecule fragments that differ in length by single nucleotides. Typically, these families of molecular fragments are separated, by electrophoresis or chromatography, and detected and analyzed to reveal the nucleic acid macromolecule sequence structure. Another example is the sequence-specific cutting of nucleic acid macromolecules by restriction endonuclease enzymes to generate a population of fragmented macromolecules which are then separated into discrete bands by electrophoresis or chromatography and detected and analyzed to reveal the sizes of the nucleic acid fragments, and so the relative positions of the restriction endonuclease cut sites. Similarly, specifically cut fragments of nucleic acid can be spliced together by a process called ligation using the enzyme ligase and the process verified by detection and analysis of the ligated fragments using electrophoresis or chromatography.

Another example is the separation and detection of populations of nucleic acid molecules generated by enzymic amplification means, such as the polymerase chain reaction (PCR) disclosed in U.S. Pat. No. 4,683,202, which allows specific nucleic acid sequences to be amplified for the purposes of detection of specific nucleic acid sequences from minute traces of starting materials.

However there are disadvantages and limitations to analyzing populations of molecular particles by electrophoresis and chromatography, in that significant amounts of molecular materials must be available to be resolved by low-resolution detection methods, the sieving materials for separation methods are expensive and the process of separation is time consuming. There is a need for rapid detection and analysis of molecular-scale particles.

Single particle detection and analysis has been achieved using scanning probe microscopes (SPMs). SPMs include the scanning tunnelling microscope (STM, See Binnig et al., "Surface studies by scanning tunnelling microscopy" *Phys. Rev. Lett*, 40, 57-61, 1982) disclosed in U.S. Pat. No. 4,343, 993 and the atomic force microscope (AFM) of U.S. Pat. No. 4,724,318. The entire contents of these patents are incorporated herein by reference. In addition to detecting particles, SPMs are capable of manipulating and controlling particles. SPMs utilize near field probes that are operated with the probes proximal to the sample of analysis. The probe-sample separation distance is set so that the electron cloud of the probe overlaps the electron clouds of the sample and the separation distance is measured by measuring a probe-sample interaction parameter. Raster scanning of the probe over the sample allows a spatial map of the interaction parameter to be plotted to reveals 'images' of the surface. The resolution of the images is dependent on the geometry of the probe and atomic scale probes can be used to reveal atomic-scale detail.

In the STM electronic circuitry senses the quantum mechanical tunnel effect between the apex of a sharpened metallic probe and a conducting surface. The probe is typically fabricated from hard metal wire, such as tungsten, and has a geometry that tapers substantially from the diameter of the wire, typically 1.0-0.1 millimetres, to an apex with a radius of curvature of the order of 10 nanometres. STM is necessarily limited to imaging electrically conducting samples, or samples coated in electrically conducting materials, thereby obscuring the molecular detail of the sample.

The atomic force microscope (AFM) of U.S. Pat. No. 4,724,318 is another type of SPM that overcomes the limitations of analyzing electrically conducting samples. Atomic scale perturbations are detected between the probe and the sample by the mechanical deflection of a raster-scanned microscopic probe attached to a cantilever. The image contrast mechanism in an AFM relies on direct physical contact between the microscopic probe and the sample and so does not require a conducting sample or probe. While modern AFMs detect deflection of a cantilever by measuring the deflection of a laser beam reflected from the cantilever surface, the AFM of U.S. Pat. No. 4,724,318 utilizes a tunnel tip attached to a z-drive in the form of a piezoelectric element.

The STM has imaged single nucleic acid macromolecules (see Guckenberger et al., "Scanning tunneling microscopy of insulators and biological specimens based on lateral conductivity of ultrathin water films" *Science,* 266, 1538-1540, 1991) and also sub-molecular components of nucleic acids, the purine (See Heckl et al "Two-dimensional ordering of the purine base guanine observed by scanning tunneling microscopy" *PNAS,* 88, 8003-8005, 1991) and pyrimidine bases (See Sowerby et al., "Scanning tunneling microscopy of uracil monolayers self-assembled at the solid/liquid interface" *J. Electroanal. Chem,* 433, 85-90, 1997). A method of STM imaging for single molecule nucleic acid sequencing has been disclosed (See Heckl et al., "DNA base sequencing" *Nonlinear Optics,* 1, 53-59, 1992) and U.S. Pat. No. 5,106,729, U.S. Pat. No. 5,270,214 and U.S. Pat. No. 5,620,854, the entire contents of which are incorporated herein by reference. However, molecular characterization by SPM is dependent on molecular resolution detection means by the SPM and suffer from the disadvantage that SPM probes are substantially short-lived and that the preferred graphite substrate used for adsorbing nucleic acid is substantially rich in artifacts which mimic DNA structure (See Clemmer et al., "Graphite: a mimic for DNA and other biomolecules in scanning tunnelling microscopy studies" *Science,* 251, 640-642, 1991).

Another type of apparatus that is available for particle analysis is the Coulter counter, as disclosed in U.S. Pat. No. 2,656,508, comprising two substantially isolated reservoirs of electrically conductive ionic fluid separated from each other by a substantially, electrically insulating barrier containing a small aperture that is the only conduit through which particles can pass between the reservoirs. Electrodes placed in each reservoir provide a means to generate a current of ions through the aperture by the application of a potential difference across the electrodes.

The effective cross-sectional area of the aperture limits the flux of ions traversing the aperture, and the length of the aperture is typically between 70 and 100 percent of the aperture diameter. Particle sensing is achieved with this configuration by utilizing a general principle known as resistive pulse sensing (See Bayley et al., "Resistive Pulse Sensing—From Microbes to Molecules" *Chem. Rev.,* 100, 2575-2594, 2000). According to this principle, the transit of a particle suspended in the ionic fluid passing through the aperture causes a resistive pulse signal in the electrical conductivity of the aperture as the particle displaces ions within the aperture, so reducing the measured current density for the period of time that the particle occupies the aperture. Studies have shown that the magnitude of the resistive pulse signal is proportional to the volume occupied by the particle within the aperture. The lower size limit for detection in these devices is reached when the particle size generates a resistive pulse signal that cannot be distinguished from the background noise of the ionic current through the aperture. Coulter-type devices are limited to detecting particles in the range of 2 percent to 60 percent of the aperture diameter, which necessitates that apertures must be fabricated for specific particle sizes. Coulter-type devices have found commercial utility analyzing particles in the range ~0.4 micrometres to ~1.0 millimetres utilizing apertures ranging in size from 20 micrometres to 2 millimetres.

U.S. Pat. No. 4,853,618 discloses a Coulter-type particle analysis apparatus in which an aperture is varied by the precisely controlled automatic insertion of an insert into the aperture so as to reduce the effective cross-sectional area of the aperture.

Coulter-type analysis of molecular scale particles has been achieved using molecular-scale apertures of biological origin. U.S. Pat. No. 5,795,782 and U.S. Pat. No. 6,015,714 disclose a method utilizing the $\alpha$-hemolysin aperture for rapid nucleic acid sequence determination and molecular characterization. Despite promising laboratory evidence, apertures based on protein pores suffer numerous disadvantages and limitations in that their formation relies on stochastic self-organization processes so that they are unpredictable and difficult to fabricate and the proteins from which they are constructed and the biological membranes into which they are inserted have short functional lifetimes.

Solid-state nanometre-scale apertures 1.5 nanometres in diameter have been fabricated in a silicon nitride membrane by focused ion beam lithography and have demonstrable DNA sensing utility (See Li et al., "Ion-beam Sculpting at Nanometre Length Scales" *Nature,* 412 166-169, 2001).

In U.S. Pat. No. 6,413,792, solid-state nanometre-scale apertures have been disclosed where utility is claimed for ultra-fast nucleic acid sequencing methods. U.S. Pat. No. 6,706,203 and US 2003/0080042 disclose an adjustable nanopore, nanotome and nanotweezer comprising two sliding solid-state crystalline or ceramic window apertures overlaid to create a single smaller aperture. However such solid-state apertures are difficult to construct and is constrained to a small window size.

SUMMARY OF THE INVENTION

According to one aspect of the present invention there is provided a particle-sensitive or radiation-sensitive device incorporating deformable material containing a deformable aperture providing a path for particles or radiation, and adjustment means for deforming the deformable material to change at least one of the parameters of the path provided by the deformable aperture.

According to another aspect of the present invention there is provided a method of detecting, measuring or controlling particles and/or electromagnetic radiation, the method comprising providing a deformable material containing a deformable aperture defining a path for particles or radiation; adjusting the deformable aperture to a prescribed geometry and/or size by deforming the deformable material to change at least one of the parameters of the path defined by the deformable aperture; and causing the particle or radiation to be detected, measured or controlled to enter the deformable aperture.

In operation of the devices and methods used to detect and/or measure and/or control the flux of matter in accordance with the present invention, control of the adjustment of the deformable aperture may be effected on the basis of parameters selected from the group comprising, but not limited to: the flux of particles traversing the deformable aperture, the flux of atomic particles traversing the deformable aperture; the flux of molecular particles traversing the deformable aperture; the flux of ionic particles traversing the deformable aperture; the flux of ionic particles in solution traversing the deformable aperture; the flux of electrical current traversing the deformable aperture, the flux of electrical tunneling current traversing the deformable aperture; and the flux of electromagnetic radiation traversing the deformable aperture. Measurable parameters of the deformable material in which the deformable aperture is fabricated may be selected from the group comprising, but not limited to: capacitance; resistance; conductivity; opacity; transparency; length; width; height; volume; thermal conductivity; and dielectric properties. Measurable parameters linked to the actuation mechanism by which the deformable aperture is adjusted may be selected from the group comprising, but not limited to: capacitance; conductivity; actuator displacement; actuator position; stepper motor position; inductance; motor coil inductance; resistance; and motor coil resistance.

BRIEF DESCRIPTION OF THE DRAWINGS

In order that the invention may be more fully understood, reference will now be made, by way of example, to the accompanying drawings, in which:

FIGS. 2a to 2f are schematic three-dimensional illustrations of deformable apertures used in embodiments of the invention;

DETAILED DESCRIPTION OF THE DRAWINGS

The following description is given by way of example with reference to embodiments of the invention utilizing polyurethane as the deformable material. However other materials that may used for the deformable material in other embodiments of the invention include but are not limited to: natural and synthetic rubbers; elastomeric materials; natural polymers, proteins, polypeptides, polysaccharides; plastics; doped conducting plastics; hydrocarbon plastics; perfluorocarbon plastics; latex materials; thermoplastic deformable materials; thermoplastic polyurethane (ethers and esters) deformable materials; olefin-based deformable materials including polypropylene, polyethylene, cyclic olefins; styrene-based deformable materials; polyamide-based deformable materials; polyester-based deformable materials; nitryl-based deformable materials; ethylene chloride copolymer cross-linked alloys; silicone deformable materials; silicate, silicon, doped silicon, or other semiconductor based materials; metals, or metal alloys. The deformable aperture can also be defined by composite deformable material made from a combination of one or more such materials.

Furthermore, modifications can be made to the deformable aperture including but not limited to chemical modifications or chemical or physical bonding of substances to the surface of the deformable aperture to render it hydrophobic, super-hydrophobic, hydrophilic, or to have specific physico-chemical properties or optical, magnetic or other physical properties. Relevant substances include, but are not limited to: chemicals; silanes; silicones. Surface modifications can also take the form of physical modifications made to the deformable material of the aperture by surface patterning to render it hydrophobic, super-hydrophobic, hydrophilic, or to have specific physico-chemical properties. The surface charge of the deformable material containing the deformable aperture can be changed by adjusting the pH of the fluid in which the deformable material is suspended, if required.

The preferred embodiment of the invention comprises at least one deformable aperture and means for detecting and measuring and controlling particles passing through the deformable aperture. To this end the device includes a deformable material containing at least one deformable aperture through which a continuous path extends from one location in the deformable material through the deformable material to another location in the deformable material, an adjustment mechanism for increasing and/or reducing deformation of the deformable material to change the geometry of the deformable aperture thereby increasing and/or reducing the diameter and/or the path length of the deformable aperture and/or changing the shape of the deformable aperture, and a feedback mechanism for monitoring and controlling the size and/or geometry of the deformable aperture.

Figure 1A:
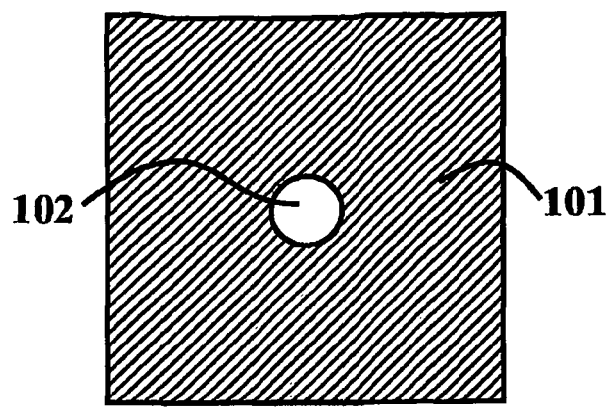
FIGS. 1a to 1c schematically illustrate two-dimensional cross-sections of deformable apertures used in embodiments of the invention.
Figure 1B:
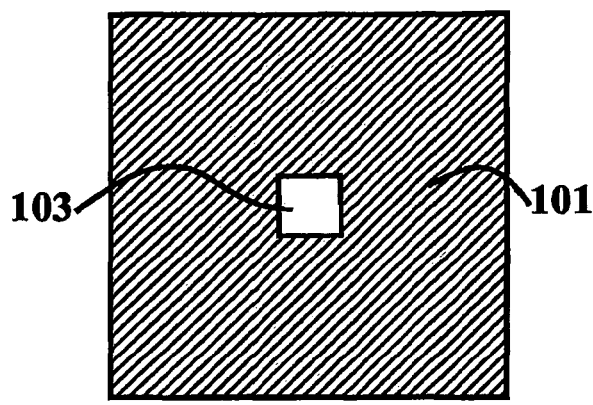
Figure 1C:
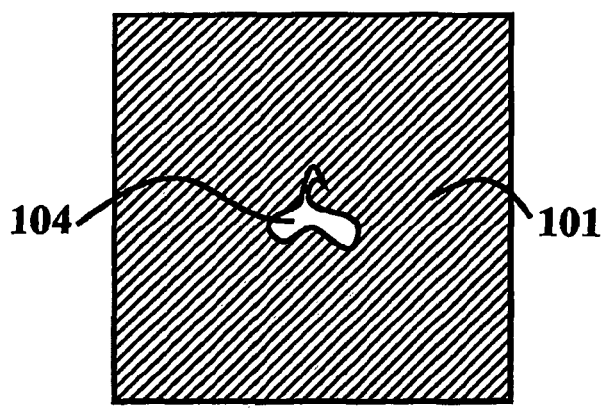

The deformable aperture is of any general three-dimensional geometry. FIG. 1a is a schematic two-dimensional cross-section through a sheet of deformable material 101 with a preferred deformable aperture cross-section 102 having a substantially regular, substantially circular geometry. FIG. 1b schematically illustrates a two-dimensional cross-section through a sheet of deformable material 101 with a preferred deformable aperture cross-section 103 having a substantially regular, substantially non-circular (i.e. square) geometry. FIG. 1c schematically illustrates a two-dimensional cross-section through a sheet of deformable material 101 with a preferred deformable aperture cross-section 104 having a substantially irregular, substantially non-circular geometry. FIG. 1a, FIG. 1b and FIG. 1c show by way of example cross-sections through either different apertures or different locations of the same aperture.

FIG. 2a schematically illustrates a preferred example 200 of a deformable aperture 201 fabricated in a deformable material 202. The bulk deformable material 202 in which the deformable aperture 201 is fabricated may be of any general shape. In FIG. 2a only a cube of deformable material 202 containing only a single deformable aperture 201 is schematically represented. However this should in no way be taken as limiting the possible shape of the bulk of the deformable material or the number of deformable apertures that may be provided in the sheet of deformable material, and it will be appreciated that the sheet may have a range of different shapes (and may not even be in the form of a sheet) and that any number of apertures may be provided in the sheet. In the bulk of the deformable material 202 there is fabricated at least one deformable aperture 201 that extends from one side 203 of the deformable material, through the deformable material to the opposing side 204 of the deformable material. In the example 200 the one deformable aperture is substantially symmetrical along the axis of the deformable aperture 201. The deformable material 202 can be deformed by mechanically acting on the deformable material along one or more of the boundaries 205, 206, 207, 208, 209 and 210 of the deformable material 202. Mechanical deformation of the deformable material 202 can be effected by one or more micrometer screw gauges extending perpendicularly to the sheet of deformable material 202, for example, and be achieved by, but should not be considered as limited to: applying tension, or compression, or torsion, or twisting, or flexing, or strain to the deformable material at one or more of the boundaries 205, 206, 207, 208, 209 and 210 of the deformable material 202.

In the preferred example 200 the deformable aperture 201 is fabricated in a body of deformable material 202 of any shape in which one or more of the three spatial dimensions of the body is less than 10 millimeters, or alternatively less than 100 microns, or alternatively less than 10 microns, or alternatively less than 100 nanometres, or alternatively less than 10 nanometres, or alternatively less than 2 nanometres.

The deformable aperture 201 preferably has an adjustable diameter of less than 2 millimeters to substantially closed, or alternatively an adjustable diameter of less than 100 microns to substantially closed, or alternatively an adjustable diameter of less than 10 microns to substantially closed, or alternatively an adjustable diameter of less than 100 nanometres to substantially closed, or alternatively an adjustable diameter of less than 10 nanometres to substantially closed, or alternatively an adjustable diameter of less than 2 nanometres to substantially closed.

The deformable aperture 201 preferably has a path length of less than 10 millimeters, or alternatively a path length of less than 5 millimeters, or alternatively a path length of less than 2 millimetres, or alternatively a path length of less than 100 microns, or alternatively a path length of less than 100 nanometres, or alternatively a path length of less than 10 nanometres, or alternatively a path length of less than 2 nanometres.

FIG. 2b schematically illustrates another example 211 of a deformable aperture 212 formed in a sheet of deformable material 213 that is substantially unsymmetrical and tapers from a large opening 214 on the upper surface 215 to a much smaller opening 216 on the opposing surface 217 of the deformable material 213. Such tapering through the deformable aperture to the other side of the deformable aperture can be of any angle ranging from 0 degrees (with substantially parallel sides as in the example 200 of FIG. 2a) to 89.99 degrees (with non-parallel sides).

FIG. 2c schematically illustrates another example 218 of a deformable aperture 219 formed in a sheet of deformable material 220 that extends between two non-opposing surfaces from an opening 221 on one surface 222 to an opening 223 on a second non-opposing surface 224 of the deformable material 220.

FIG. 2d schematically illustrates another example 225 of a deformable aperture 226 formed in a sheet of deformable material 227 that extends from an opening 228 on one surface 229 to an opening 230 on the same surface 229 of the deformable material 227.

FIG. 2e schematically illustrates another example 231 in which the path of the deformable aperture 232 within the deformable material 233 is convoluted.

FIG. 2f schematically illustrates another example 234 in which the diameter of the path of the deformable aperture 235 within the deformable material 236 is substantially irregular.

It will be appreciated that the examples given above are non-limiting in their scope and that variations of deformable apertures combining one or more of the above described examples can also be used in embodiments of the invention.

Figure 3A:
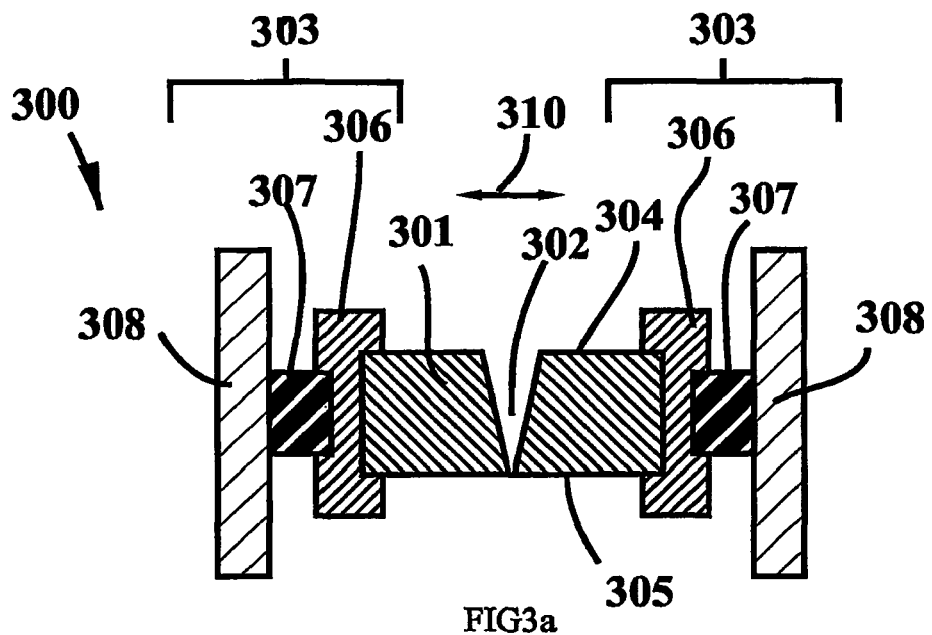
FIGS. 3a to 3b are schematic sectional and plan views of a deformable aperture to be mechanically deformed in an embodiment of the invention.
Figure 3B:
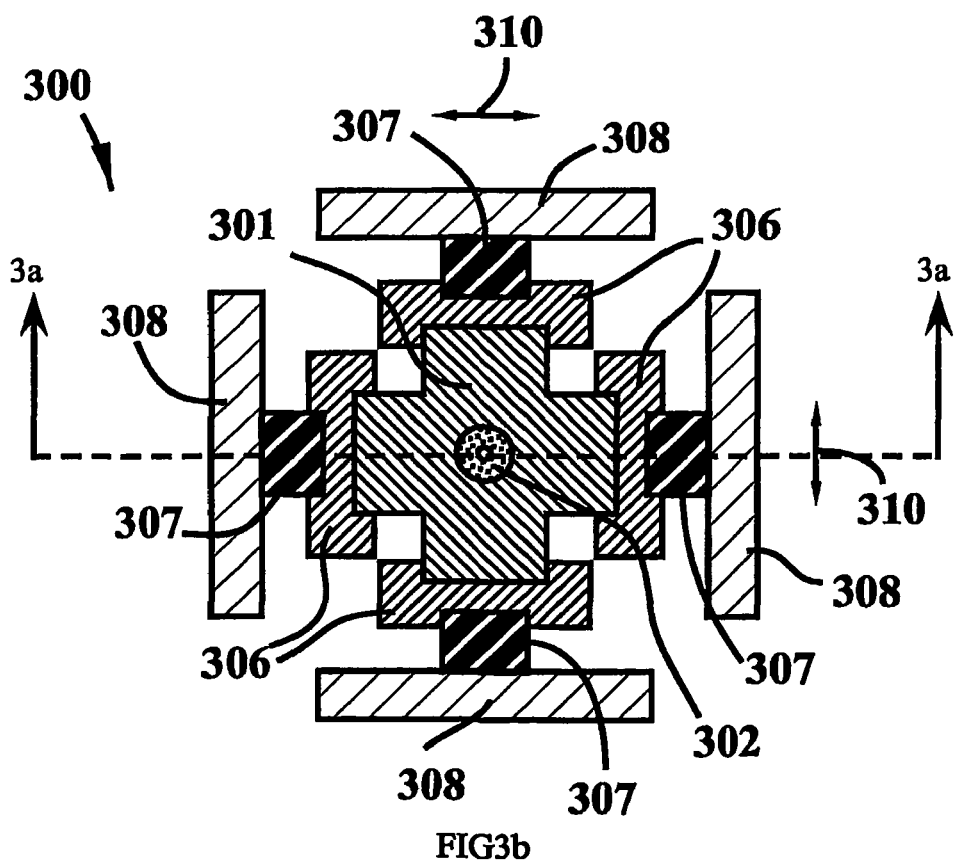

FIG. 3a and FIG. 3b schematically illustrate a preferred example 300 of a device according to the present invention in which a sheet of deformable material 301 containing at least one deformable aperture 302 is mechanically deformable by a machine 303.

FIG. 3a is a cross-sectional view of the device, whereas FIG. 3b is a plan view of the device, with the cross-section of FIG. 3a being taken along the dashed line 3a-3a of FIG. 3b.

The device of FIGS. 3a and 3b comprises a sheet of the deformable material 301 having an upper surface 304 and a lower surface 305. As best seen in the plan view of FIG. 3b, the sheet of deformable material 301 is formed with a central deformable aperture 302 and is of a cruciform geometry, and the opposing edges of the cruciform shaped sheet are held firmly by clamps 306. Other possible means for holding the deformable material comprise, but are not limited to, clasps, claws, grips or adhesives. The deformable material may also incorporate attachment mechanisms fabricated within the material. Preferred examples include, but are not limited to, lugs, eyelets or hooks. The clamps 306 attach the deformable material 301 to mechanical actuators 307 mounted on the casing 308 of the machine 303. The mechanical actuators 307 of the machine 303 serve to vary the deformation of the deformable material 301.

The mechanical deformation of the deformable material 301 by the machine 303 thereby serves to adjust the deformable aperture 302. The machine can be adapted to effect mechanical deformation in the range of 0 to 50 millimeters, or in the range of 0 to 10 millimetres, or in the range of 0 to 1 millimetres, or in the range of 0 to 100 microns, or in the range of 0 to 1 microns, or in the range of 0 to 100 nanometres or in the range of 0 to 1 nanometers. Depending on the degree of deformation required, the adjustment mechanism can be selected from the group, but not limited to, one or more of: mechanical actuators; electromagnetic actuators; electrostatic actuators; piezoelectric actuators; pneumatic actuators; hydraulic actuators; thermo mechanical actuators, centrifugal actuators gravitational actuators; and acoustic actuators. The deformable material may also have deformation actuation mechanisms fabricated within the material. Preferred examples include, but are not limited to, thermoresponsive elements and magnetic elements.

The cross-section of FIG. 3a shows only one axis of deformation, as indicated by the double-headed arrow 310. However the plan view of FIG. 3b shows that deformation of the deformable material 301 can be performed along two mutually orthogonal axes by adjusting the deformation applied at the opposing edges of the cruciform shaped sheet, as indicated by the double-headed arrows 310. It will be appreciated that, by adjusting the deformation of the deformable material 301 by actuation of the actuators 307, it is possible to adjust the geometry of the deformable aperture 302. The mechanical actuators 307 can apply deformation to the deformable material 301 in an isotropic manner by acting substantially symmetrically in their mode of operation with deformation applied substantially equally to the two axes of the cruciform geometry of the deformable material 301, thereby changing the size of the deformable aperture 302 by uniformly opening and closing the deformable aperture 302. Alternatively, the mechanical actuators 307 can apply deformation to the deformable material 301 in an anisotropic manner by acting asymmetrically in their mode of operation with deformation applied unequally to the two axes of the cruciform geometry of the deformable material 301 thereby changing the shape and/or size of the deformable aperture 302.

Another embodiment of device according to the present invention (not shown) comprises a sheet of deformable material of triangular shape with deformation applied equally or unequally to the three edges of the triangle. Another embodiment of device according to the present invention (not shown) comprises a sheet of deformable material of rectangular shape with deformation applied equally or unequally to one up to four edges of the rectangle. Another embodiment of device according to the present invention (not shown) comprises a sheet of deformable material of oval shape with deformation applied equally or unequally to the circumference of the oval. Another embodiment of device according to the present invention (not shown) comprises a sheet of deformable material of circular shape with deformation applied equally or unequally to the circumference of the circle. In a general example (not shown) the sheet of deformable material can be a polygon of n sides with deformation applied equally or unequally to one or more, up to n, edges of the polygon.

Figure 4A:
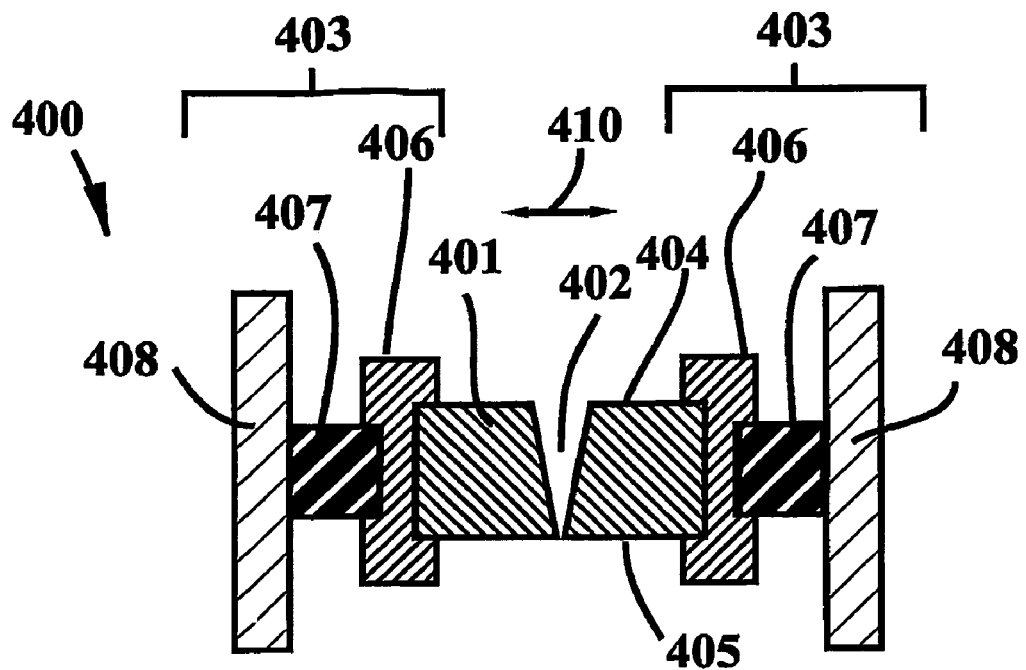
FIGS. 4a to 4b are schematic sectional views of a deformable aperture in two different opening positions in an embodiment of the invention.
Figure 4B:
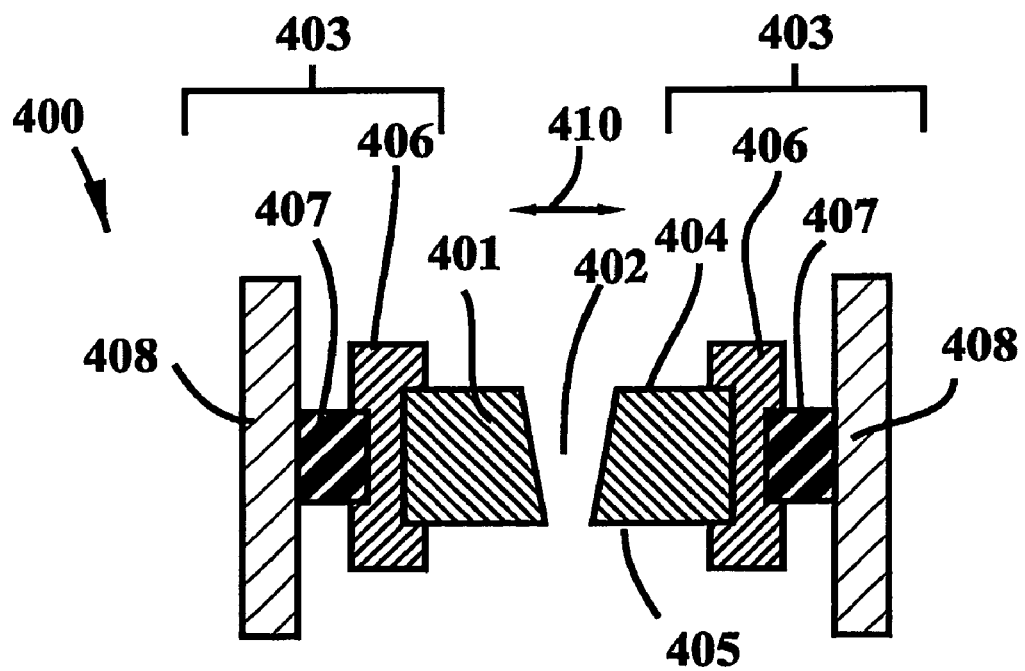

FIGS. 4a and 4b schematically illustrate two cross-sectional views of an exemplary device 400 according to the present invention that is generally similar to the device 300 of FIG. 3a. As shown in FIGS. 4a and 4b, the device 400 incorporates a sheet of deformable material 401 incorporating a central deformable aperture 402 and having an upper surface 404 and a lower surface 405 with the opposing edges of the deformable material 401 being held firmly by clamps 406 of a machine 403. The clamps 406 attach the deformable material 401 to mechanical actuators 407 mounted on the casing 408 of the machine 403. The mechanical actuators 407 provide variable deformation of the deformable material. As illustrated in FIGS. 4a and 4b, the deformable aperture 402 is narrow in the adjustment position shown in FIG. 4a as compared to the adjustment position shown in FIG. 4b in which, due to the action of the mechanical actuators 407, the deformable aperture 402 has been caused to open in the direction indicated by the double-headed arrow 410.

Embodiments of the present invention include particle-sensitive devices for sensing, counting, characterizing, clamping and/or gating particles using a single deformable aperture in conjunction with an ionic solution of, for example, potassium chloride electrolyte as described below by way of example. This provides precise control of the voltage potential difference across a deformable aperture coupled with sensitive single channel recording measurements and a precise electromechanical adjustment mechanism for adjusting the deformation of the deformable material controlled by a series of electronic circuits and a computer.

Ionic solutions includes solutions prepared from materials selected from the group comprising, but not limited to: fluids; liquid fluids; fluids that are of pure composition; fluids that are mixtures of materials; aqueous fluids; water; salts; inorganic salts; organic salts; electrolytes; chemical acids; chemical bases; chemical zwitterions; detergents; buffers; proteins; alcohols; organic solvents; and polar solvents.

The fact that many particles exhibit natural electro-active character in an electric field allows the direction and rate of passage of the particle through the deformable aperture to be controlled by the size and polarity of the applied potential difference across the deformable aperture. Electro-activity within an ionic solution is conferred by the overall charge on each particle and so can be modified by the pH of the electrolyte. It is thus possible to cause a particle to enter and/or traverse and/or reverse and/or exit the deformable aperture at prescribed rates by applying the appropriate potential difference across the deformable aperture.

In this example, the monitoring of the ion flux through the deformable aperture relies on an established technique, namely single channel recording (See Bayley et al., "Resistive Pulse Sensing—From Microbes to Molecules" *Chem. Rev.*, 100, 2575-2594, 2000). When a potential difference is established across the deformable material containing the deformable aperture, a steady current of ions flows through the deformable aperture from one side of the deformable material to the other side of the deformable material. The steady flow of ions can be measured by conventional single channel recording techniques. We have established that the minimum cross-sectional area of the deformable aperture does in part limit the flux of ions flowing through the deformable aperture so that adjustment of the deformable aperture results in concomitant adjustment to the flux of the ions flowing through the deformable aperture as measured by conventional single channel recording techniques.

Figure 5:
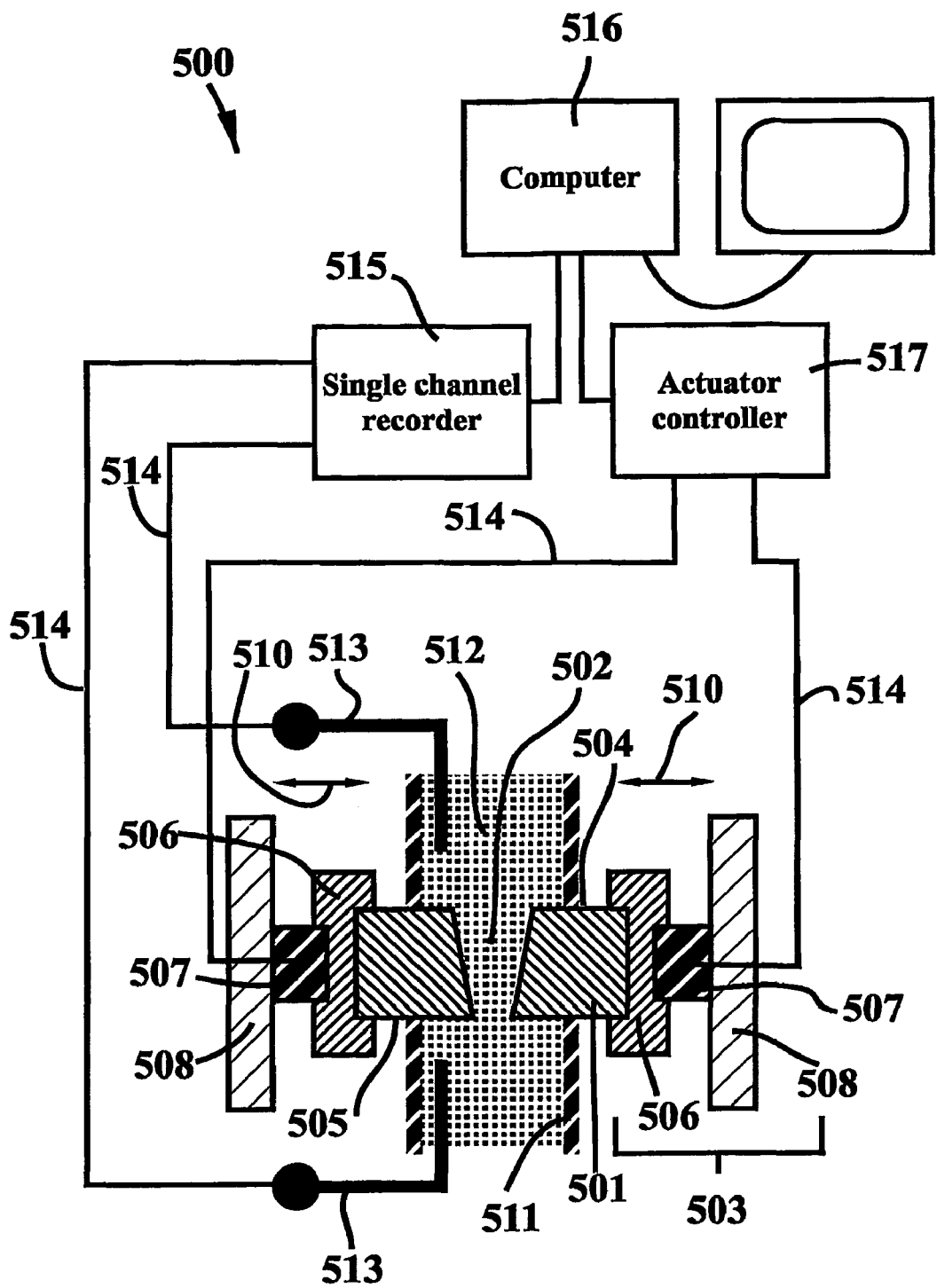
FIG. 5 schematically illustrates a preferred embodiment of the invention including an arrangement for monitoring the size of the deformable aperture.

FIG. 5 schematically illustrates an exemplary device 500 according to the present invention incorporating a sheet of deformable material 501 containing a central deformable aperture 502 arranged to be mechanically deformed by a machine 503. The sheet of deformable material 501 has an upper surface 504 and a lower surface 505. The opposing edges of the sheet of deformable material 501 are held firmly by clamps 506. The clamps 506 attach the deformable material 501 to mechanical actuators 507 mounted on the casing 508 of the machine 503. The mechanical actuators 507 are adapted to vary the deformation of the deformable material 501. The mechanical deformation of the deformable material 501 by the machine 503 effects variable adjustment of the deformable aperture 502, as indicated by the double-headed arrows 510. The arrangement includes a mechanism for monitoring the size of the deformable aperture 502 consisting of a boundary 511 for holding a volume of ionic fluid 512, preferably an aqueous solution containing potassium chloride, and electrodes 513 preferably of silver chloride within the fluid volume. The electrodes 513, which could alternatively be made from platinum, gold, tungsten or some other conducting or semi-conducting substance, confer the ability to monitor the ionic current through the deformable aperture 502 by electrical connectors 514 to a single channel recording apparatus 515. The single channel recording apparatus 515 is preferably coupled via a programmable logic device 516 to a mechanism for controlling an actuator 517 for adjusting the size of the deformable aperture 502.

In FIG. 5 the source of ionic current through the ionic solution 512 passing through the deformable aperture 502 is a voltage source applied across the deformable aperture 502 through the electrodes 513 prescribed by the single channel recording apparatus 515 by way of software algorithms (not shown) executed on the programmable logic device 516. Electronic current amplifiers within the single channel recording apparatus 515 detect the flux of ions passing through the deformable aperture 502 by single channel recording techniques.

The monitoring of the ion current flux through the aperture by single channel recording techniques is an inexpensive, viable method that has been used widely since the invention of the Coulter counter. Modern single channel recording instruments are sensitive enough to detect and record the movements of single ions taking place in the range of a few microseconds to milliseconds and comprise single channel recording instrumentation which can apply a variable range of voltages from about +1000 millivolts to about −1000 millivolts across the deformable material containing the aperture, a very low-noise current amplifier and current injector; and analog to digital converters (ADCs) that can be interfaced to digital electronic computers using data acquisition software and electronic storage media (e.g. computer disk, magnetic tape). Equipment meeting these criteria is readily available, such as from Axon Instruments, Union City, Calif., USA (e.g. Axopatch 200B systems; pClamp 9.0 software).

As shown in FIG. 5, a feedback loop is established for controlling the size of the deformable aperture by utilizing the above described single channel recording apparatus 515, a programmable logic device 516 and the actuator controller mechanism 517.

The actuator controller mechanism 517 controls the deformation of the deformable aperture 502 by deforming the deformable material 501 by electromechanical actuation of the deformable material 501 through the clamps 506 attaching the deformable material 501 to actuators 507 mounted on the casing 508 of the machine 503. Instrumentation is required which can apply a variable amount of actuation, from 0 to 50 millimetres with a lateral precision of less than one nanometre, and that can be electronically controlled via digital to analog converters (DACs) interfaced to digital electronic computers using control and data acquisition software and electronic storage media (eg. computer disk, magnetic tape). Equipment meeting these criteria is readily available, such as from Physik Instrumente, Karlsruhe, Germmany (e.g. M-168 High Resolution Stepper Mike Actuators, P-250.20 High Resolution PZT Micrometer Tip; C600 Motor Controller and PZT Drivers; customized software). The adjustment mechanism for adjusting the deformation of the aperture is computer controllable, thus allowing for the degree of deformation to be prescribed by algorithms.

Figure 6:
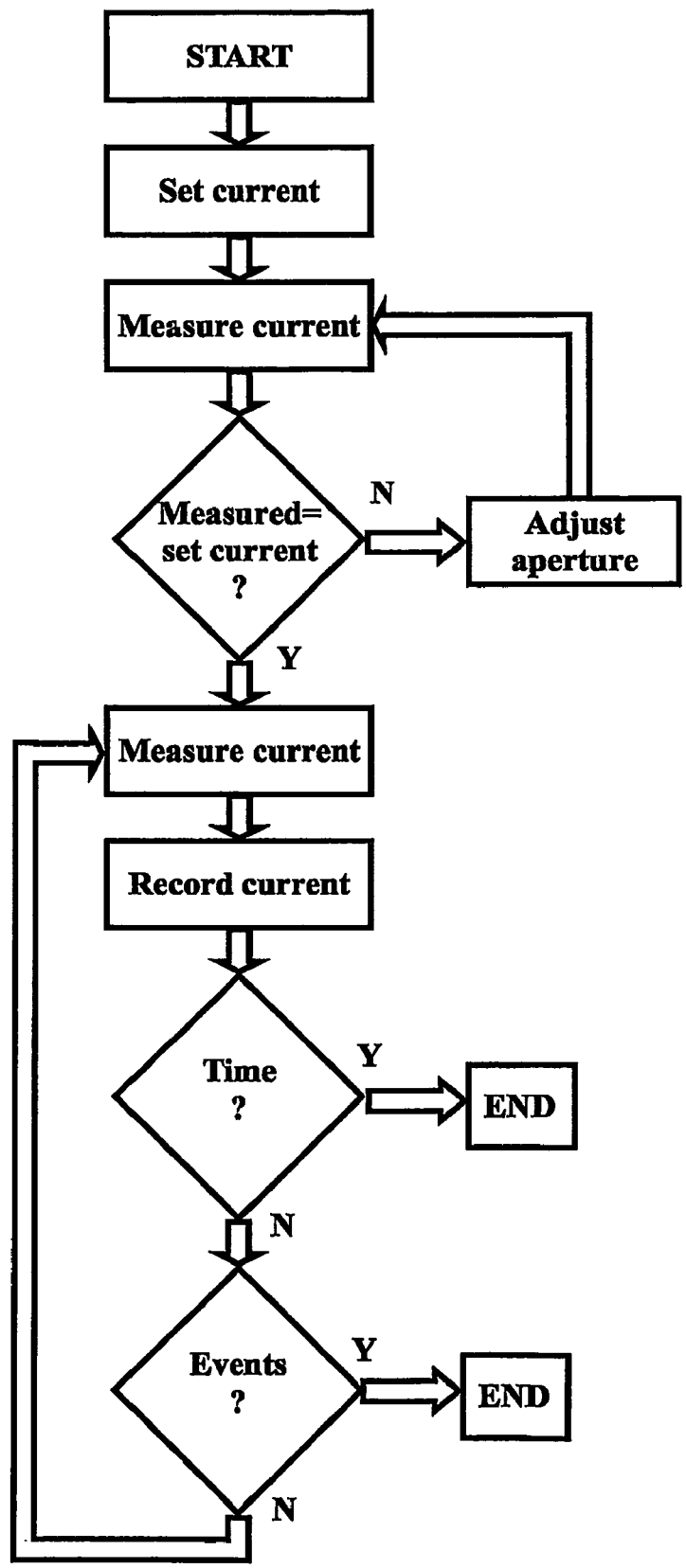
FIG. 6 is a flow chart depicting one possible mode of operation of the embodiment illustrated in FIG. 5.

FIG. 6 is a flow chart depicting one exemplary mode of operation of the device of FIG. 5.

Prescriptive mode: Operation is performed by setting at least one parameter of the deformable aperture according to a predefined algorithm. Changes in at least one measured parameter arising from at least one particle entering and/or traversing and/or exiting the deformable aperture are recorded and used for interpretation. It will be appreciated that sensing of at least one single particle completely traversing the deformable aperture provides a single incremental count event for at least one single particle which is repeated until a statistically significant period of time or statistically significant number of particles have been detected and counted to determine the number of particles per unit volume. Exit conditions are also provided for time based and event based data accumulation. In FIG. 6, "TM?" designates the logical condition that tests whether the current analysis time exceeds a predefined analysis duration. In FIG. 6, "EVENT?" designates the logical condition that tests whether the current analysis of enumerated counting events exceeds a predefined number of counting events to be detected.

Figure 7:
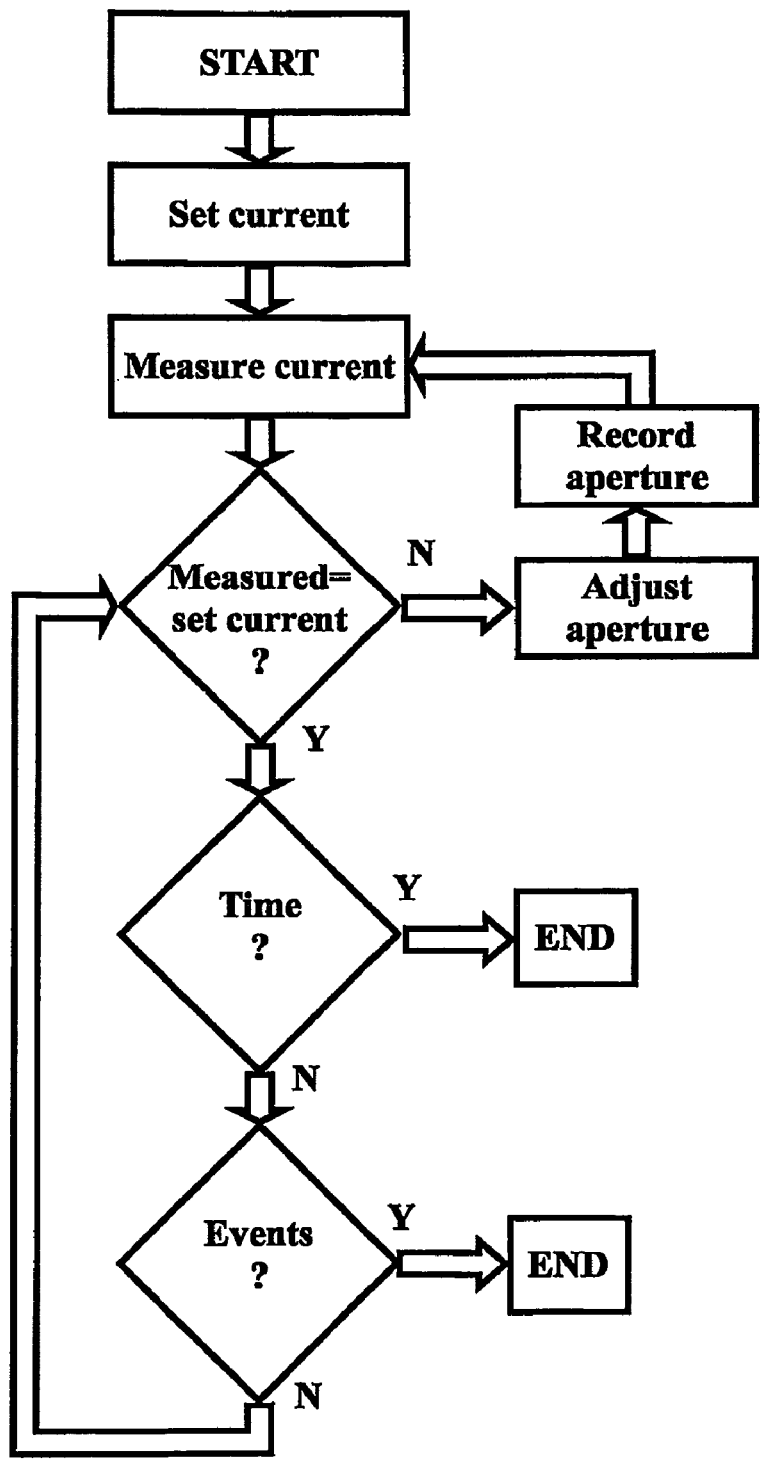
FIG. 7 is a flow chart depicting another possible mode of operation of the embodiment illustrated in FIG. 5.

FIG. 7 is a flow chart depicting another exemplary mode of operation of the device of FIG. 5.

Reactive mode: Operation is performed by applying a feedback signal of a measured parameter of the deformable aperture, set to a pre-defined set-point level according to a pre-defined algorithm consisting of at least one predefined set-point level in which the size and/or geometry of the deformable aperture responds to the feedback signal of the measured parameter to maintain the at least one predefined set-point level of the measured parameter. Changes in the size and/or geometry of the deformable aperture and/or other measurable parameters of the deformable aperture and/or actuation mechanism by which the deformable aperture is adjusted are recorded and used for interpretation.

It will be appreciated that sensing of at least one single particle completely traversing the deformable aperture provides a single incremental count event for at least one single particle which is repeated until a statistically significant period of time or statistically significant number of particles have been detected and counted to determine the number particles per unit volume. Exit conditions are also provided for time based and event based data accumulation. In FIG. 7, "TIME?" designates the logical condition that tests whether the current analysis time exceeds a predefined analysis duration. In FIG. 7, "EVENT?" designates the logical condition that tests whether the current analysis of enumerated counting events exceeds a predefined number of counting events to be detected.

The deformable aperture of the present invention includes a mechanism for monitoring deformation of the deformable material. In one general example of the device of the invention, the mechanism for monitoring the deformation of the deformable material preferably includes the ability to monitor the degree of actuation by the actuators and is preferably coupled to the mechanism for adjusting deformation of the deformable material to create a feedback loop for controlling the deformation of the deformable material. The feedback loop is selected from the group comprising, but not limited to, analog feed back loops, electronic feedback loops and computer controlled feedback loops.

In another general example of the device of the invention, the mechanism for monitoring the deformation of the deformable material preferably includes the ability to monitor a physical property of the deformable material from the group, but not limited to: capacitance; resistance; conductivity; opacity; transparency; length; width; height; volume; thermal conductivity; dielectric properties; and is preferably coupled to the mechanism for adjusting deformation of the deformable material to create a feedback loop for controlling the deformation of the deformable material. The feedback loop is selected from the group comprising, but not limited to, analog feed back loops, electronic feedback loops and computer controlled feedback loops.

In another general example of the device of the invention, the mechanism for monitoring the deformation of the deformable material preferably includes the ability to monitor the geometry of the deformable aperture. In one specific example of the invention the mechanism for monitoring the geometry of the deformable aperture includes the ability to monitor the flux of particles and/or electromagnetic radiation passing through the deformable aperture, and is preferably coupled to the mechanism for adjusting the size of the deformable aperture to create a feedback loop for controlling the size of the deformable aperture. The feedback loop is selected from the group comprising, but not limited to analog feed back loops, electronic feedback loops and computer controlled feedback loops.

The deformable aperture is set to at least one prescribed geometry by applying deformation of at least one prescribed type to the adjustment mechanism for adjusting the deformation to the deformable aperture by applying at least one prescribed signal to the adjustment mechanism. The prescribed signals applied to the adjustment mechanism are preferably selected from the group comprising, but not limited to: mechanical devices; analog electronic circuits; digital electronic circuits and computer-controlled circuits.

The deformable aperture is set to at least one prescribed geometry for at least one prescribed period of time by applying deformation of at least one prescribed type to the adjustment mechanism for adjusting the deformation to the deformable aperture by applying at least one prescribed signal to the adjustment mechanism for at least one prescribed period of time. The prescribed signals applied to the adjustment mechanism are preferably selected from, but not limited to, the group comprising mechanical devices, analog electronic circuits, digital electronic circuits and computer-controlled circuits.

The sub-nanometre precision of the adjustment mechanism for adjusting the deformable aperture is coupled via a computer-controlled feedback loop to the single channel recording instrumentation and allows for the deformable aperture to be adjusted so as to be capable of controlling, detecting and recording the movements of single ions.

Figure 8A:
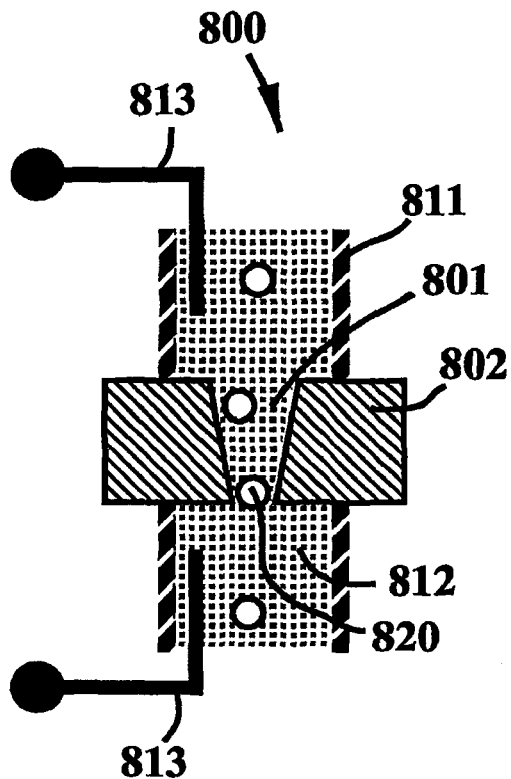
FIGS. 8a to 8c are simplified schematic illustrations of operational steps in use of the embodiment illustrated in FIG. 5.
Figure 8B:
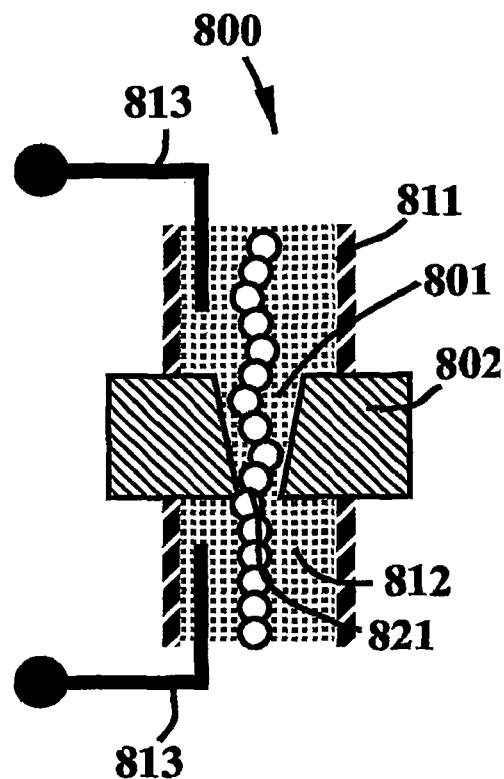
Figure 8C:
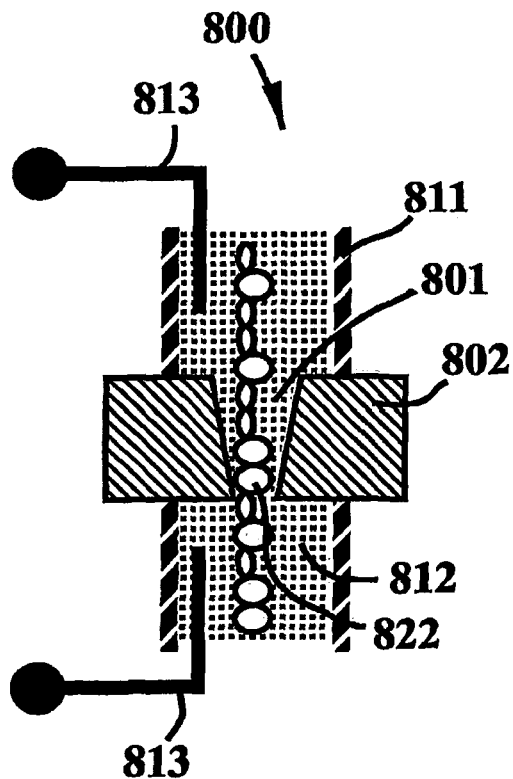

FIG. 8a, FIG. 8b and FIG. 8c show simplified schematic illustrations of a device 800 similar to the device 500 shown in FIG. 5.

In these figures, a deformable aperture 801 is fabricated within a sheet of deformable material 802, and a boundary 811 is provided for holding a volume of ionic fluid 812, for example an aqueous solution of potassium chloride, in which sit electrodes 805 of, for example, silver chloride. By comparison to FIG. 5 it will be appreciated that the ability to monitor the ionic current through the deformable aperture 801 is coupled via a programmable logic device (not shown) to a single channel recording apparatus (not shown) and to the mechanism for controlling the actuator (not shown) for adjusting the size of the deformable aperture 801. Thus, a computer controlled feedback loop allows the deformable aperture 801 to be adjusted according to the conductance of the deformable aperture 801 and allows for the degree of deformation and/or the conductance of the deformable aperture 801 to be prescribed by specific algorithms. It will also be appreciated that the voltage across the deformable aperture 801 applied through the silver chloride electrodes 813 can be precisely controlled at the level of the programmable logic device (not shown) connected by electrical connectors (not shown) to a single channel recording apparatus (not shown) which is in turn connected by electrical connectors (not shown) to the silver chloride electrodes 813, and can thus be set and/or varied in response to specific events or stimuli, or according to at least one predefined algorithm.

The device 800 is particularly useful for detecting and/or measuring and/or controlling the flux of one or more particles 820 through the deformable aperture, as shown in FIG. 8a, the particles 820 being selected from the group comprising, but not limited to: inorganic particles; organic particles; magnetic particles; silica particles; sepharose particles; styrene particles; metal particles; colloidal particles; particles conjugated to molecules; particles conjugated to biological molecules; particles conjugated to immunoglobulins; particles conjugated to nucleic acids; biological particles; biological cells; blood cells; spermatozoa; oocytes; microbiological cells; bacterial cells; fungal cells; viruses; sub-cellular organelles; mitochondria; nuclei; chloroplasts; lysosomes; ribosomes; atomic particles; ionic particles; and molecular particles.

In one example a particle counter is provided operating in the reactive mode of operation. An ionic electric current is set to a pre-defined set-point level across the deformable aperture 801 by a voltage applied across the deformable aperture 801 applied through the silver chloride electrodes 813 according to a predefined algorithm consisting of, at least one, pre-defined set-point level. The applied voltage establishes an electric field within the boundaries 811 that confine the electrolyte 812 and in which the field strength is concentrated through the aperture 801. The particles 820 are caused electrophoretically to enter and then occlude the deformable aperture 801. In doing so they reduce the volume of potassium chloride electrolyte 812 in the aperture 801 and so limit the flux of measured ionic current. In this mode, the changing feedback signal of the measured ionic current causes the size and/or geometry of the deformable aperture 801 to respond and to maintain the set-point level of the ionic current. As the particle 820 exits the deformable aperture 801, the volume of potassium chloride electrolyte 812 in the aperture 801 increases and so the flux of measured ionic current is increased. The changing feedback signal of the measured ionic current causes the size and/or geometry of the deformable aperture 801 to respond and to maintain the set-point level of the ionic current. Changes in the size and/or geometry of the deformable aperture 801 are recorded and enumerated to determine the number of particles per unit volume.

In another example a particle counter is provided operating in the prescriptive mode of operation. A voltage is applied through the silver chloride electrodes 813 across the deformable aperture 801 preset to a suitable size and/or geometry. Changes are produced in the ionic current signal as particles 820 occlude the deformable aperture 801, thus reducing the volume of potassium chloride electrolyte 812 within the deformable aperture 801, and these changes are recorded directly and enumerated to determine the number of particles per unit volume.

The device 800 is particularly useful for detecting and/or measuring and/or controlling the flux of one or more particles 821 through the deformable aperture, as shown in FIG. 8b, the particles 821 being selected from the group comprising, but not limited to: particles that are polymers; nucleic acids and chemical modifications thereof, deoxyribose nucleic acids and chemical modifications thereof, ribose nucleic acids and chemical modifications thereof; protein polymers and chemical modifications thereof; carbohydrate polymers and chemical modifications thereof.

The device 800 is particularly useful for detecting and/or measuring and/or controlling the flux of one or more particles 822 through the deformable aperture, as shown in FIG. 8c, the particles 822 being selected from the group comprising, but not limited to: particles of nucleic acids and chemical modifications thereof, deoxyribose nucleic acids and chemical modifications thereof, ribose nucleic acids and chemical modifications thereof.

In this example, reference will be made to the application of this device for characterizing biological polymers such as: deoxyribose nucleic acids (DNA) and chemical modifications thereof; ribose nucleic acids (RNA) and chemical modifications thereof, although other polymers may also be characterized.

This example is particularly well suited to the characterization of individual polymer molecules, although it is equally well suited to the characterization of homogeneous preparations of heteropolymer molecules of the same length, as well as heterogeneous mixtures of molecules, leading to a characterization of the polymer mixture for polymer length distribution, polymer copy number and polymer sequence structure.

One embodiment of the invention is provided for determining DNA length distribution and copy number generated by DNA restriction digest. DNA length distribution relates to the number of monomeric subunits per strand and the distribution of these within the total population of strands, and copy number relates to the absolute concentration of specific DNA fragments. Purified DNA derived from genomic sources or cloned DNA can be digested using a suitable restriction endonuclease. For example, digestion of 100 nanograms of purified DNA may be effected in 20 microlitres of buffer containing 150 millimolar NaCl, 60 millimolar Tris-HCl pH 7.9 and 5 units of BamHI restriction endonuclease. After digestion and heat inactivation of the restriction endonuclease, cohesive termini are removed by digestion with mung-bean nuclease or klenow DNA polymerase, eliminating elongated blockade events associated with cohesion of multiple fragments. The deformable aperture size can be adjusted to the appropriate cross sectional area by deforming the deformable aperture to achieve a predetermined ionic flux under standard operating conditions for DNA analysis (eg 1 molar KCl, 10 millimolar Tris-HCl pH 8.0, 1 millimolar EDTA: 120 millivolts bias). The deformable aperture can be pre-calibrated with known linear DNA standards eg 1-48 kilobases etc. The fragment sizes from the restriction digest can then be analyzed by examination of single channel recordings for linear translocation events.

In another embodiment of the invention provided for determining DNA length distribution and copy number generated by DNA ligation reaction, linear DNA fragments derived from restriction enzyme digestion of genomic DNA can be ligated into plasmid vector DNA. Typically 50 nanograms of de-phosphorylated vector DNA can be ligated with 150 nanograms of insert DNA in a buffer containing 50 millimolar Tris-HCl, pH 7.8, 10 milimolar $MgCl_2$, 10 millimolar dithiothreitol, 1 millimolar adenosine triphosphate, 25 microgram/millilitre bovine serum albumin and 10 units of T4 DNA ligase. The deformable aperture can be adjusted to the appropriate cross sectional area by deforming the deformable aperture to achieve a predetermined ionic flux under standard operating conditions for DNA analysis (eg 1 molar KCl, 10 milimolar Tris-HCl pH 8.0, 1 millimolar EDTA: 120 millivolts bias). The deformable aperture can be pre-calibrated with known linear DNA standards eg 1-48 kilobases etc. The fragment sizes from the restriction digest can then analyzed by examination of single channel recordings for linear translocation events. Circular double stranded DNA produces blockade events equivalent to the translocation of two parallel lengths of double stranded DNA, so that circularized DNA products of the ligation would be distinguishable from the precursor linear double stranded DNA and vector by blockade current depth. The duration of the blockade event would identify the product size, distinguishing any vector circularization from vector-insert circularization.

In another example a method is provided for determining DNA length distribution and copy number generated by polymerase chain reaction (PCR). Polymerase chain reactions can be performed under standard conditions eg 50 millimolar KCl, 10 millimolar Tris-HCl pH 8.3, $MgCl_2$ (1-2.5 millimolar), dNTP's (2.5 millimolar), forward and reverse primers 2.5 micromolar, template DNA 100 nanograms and Taq DNA polymerase 0.25 units. The times and temperature of each step (denaturing, annealing, extension) in the cycle can be optimized for individual primer sets. Cycles could range from 1 to 10 cycles, or from 1 to 40 cycles. The deformable aperture size can be adjusted to the appropriate cross-sectional area by deforming the deformable aperture to achieve a predetermined ionic flux under standard operating conditions for DNA analysis (eg 1 molar KCl, 10 millimolar Tris-HCl pH 8.0, 1 millmolar EDTA: 120 millivolts bias). The deformable aperture can be pre-calibrated with known linear DNA standards eg 1-48 kilobases etc. The fragment sizes from the restriction digest can then be analyzed by examination of single channel recordings for linear translocation events. Characterization of the products of the PCR reaction products can distinguish single stranded primers (shallow blockade events) from double stranded products. Primer dimers, being substantially smaller than the correct PCR product, are distinguishable by single channel recording measurements. Translocation of template DNA would be rare, because of the low copy number relative to the abundant PCR product. The above described method offers significant advantages over standard PCR techniques as the sensitivity of detection offered by the device of the invention requires fewer than 10 cycles to detect the product.

Such characterization is also useful for determining DNA length distribution and copy number of nucleic acid fragments generated by, but not limited to: DNA exonuclease digestion; reverse transcriptase polymerase chain reaction; DNA polymerase with chain terminating inhibitors (Sanger sequencing); chemical digestion (Maxam-Gilbert sequencing). The speed of the method and the size of the molecular fragments that can be characterized is of particular advantage since the device of the invention relies on the direct high-speed characterization of individual DNA molecules rather than the separation of polymers as in the case of methods utilizing mass spectroscopy, gel electrophoresis, or chromatographic methods. Furthermore, the methods of characterization of the invention are direct and can be applied not only to cloned DNA molecules but also to DNA molecules extracted directly from living tissue, and so offers the advantage of being able to determine the position of modified DNA bases such as 5-methyl cytosine, which has an important regulatory role in eukaryotic cell types.

In another example, polymer characterization provides easy and rapid determination of DNA length distribution, copy number and polymer sequence. Polymer sequence relates to the specific sequential order of monomeric subunit residues, which comprise the polymer chain. Polymer length distribution relates to the number of monomeric subunits per strand and the distribution of these within the total population of strands, and copy number relates to the absolute concentration of specific DNA fragments. For nucleic acids, in particular DNA, the monomeric subunit residues comprise a set of four molecular groups called mononucleotides. More specifically the four mononucleotides are called deoxyguanosine mononucleotide (G), deoxyadenosine mononucleotide (A), thymidine mononucleotide (T), deoxycytidine mononucleotide (C) (See Alberts et al (1994) "*Molecular Biology of the Cell*", Garland publishing, Inc., NY.).

In the prescriptive mode of operation as described above and illustrated in FIG. 6, the deformable aperture can be tuned to function as a means for determining the length distribution and/or the monomer subunit sequence of DNA molecules and other polymers as disclosed in U.S. Pat. No. 6,015,714. In this method, the molecular volume of the translocating DNA monomer subunit perturbs the ionic flux of the aperture. The DNA monomer subunit molecular volumes are different and sequential translocation within the fixed geometry of an aperture occludes the aperture in a sequence dependent way. The concomitant change in the measured ionic flux of the aperture due to the co-translocating ions allows the sequential presence of monomer subunits to be recorded, preferably by electronic means, and used for interpretation of the DNA length distribution, copy number and/or sequence structure.

In another example under the reactive mode of operation as described above and illustrated in FIG. 7, the deformable aperture can be tuned to function as a means for determining the length distribution and/or the monomer subunit sequence of DNA molecules and other polymers. The concomitant change in the measured ionic flux of the aperture due to the sequential presence of translocating DNA monomer subunits and co-translocating ions allows feedback driven changes in the geometry of the deformable aperture to be recorded, preferably by electronic means, and used for interpretation of the DNA length distribution, copy number and/or sequence structure.

In another example of DNA monomer sequence determination, both prescriptive and reactive current modes of operation can be used interchangeably. For example in the reactive mode, the detection of a DNA polymer within the aperture by the concomitant change in the measured ionic flux of the aperture can be used to apply the appropriate electronic signal for deformation of the aperture geometry to a new ionic flux level and can thus effect clamping of the DNA polymer as it traverses the aperture.

The application of a second appropriate electronic signal for deformation of the aperture geometry to a new ionic flux level can effect release of a clamped DNA polymer to allow it to traverse the aperture. Deformation of the deformable aperture can be used for clamping a DNA polymer and for releasing it in a precisely controlled and sensitive manner.

Furthermore, by precisely controlling the size and polarity of the applied potential difference across the deformable aperture in conjunction with precise electromechanical actuation of the aperture, it is possible to apply prescribed signals that facilitate cycles of shunting and clamping of a DNA polymer through the deformable aperture. The magnitude of the shunting-clamping cycles thus allows a DNA polymer to be ratcheted through the deformable aperture in one direction or in the reverse direction. The concomitant translocation of ions yields a detectable change in the ion flux that can be recorded, preferably by electronic means, and used for interpretation.

The signals that facilitate the clamping component of the ratcheting of the DNA polymer through the deformable aperture can be applied through the same electromechanical deformation mechanism that prescribes the geometry of the deformable aperture. Alternatively it can be applied through additional quite separate actuators that either directly deform the aperture through, for example, electromechanical means or indirectly deform the aperture through, for example, acoustic means.

The precisely combined signals of aperture deformation and potential difference which facilitate the ratcheting of a DNA polymer through the deformable aperture can be set to incrementally ratchet as little as a single monomer subunit which corresponds to a lateral translocation of the DNA molecule of between 0.36-0.70 nanometres through the deformable aperture.

Figure 9:
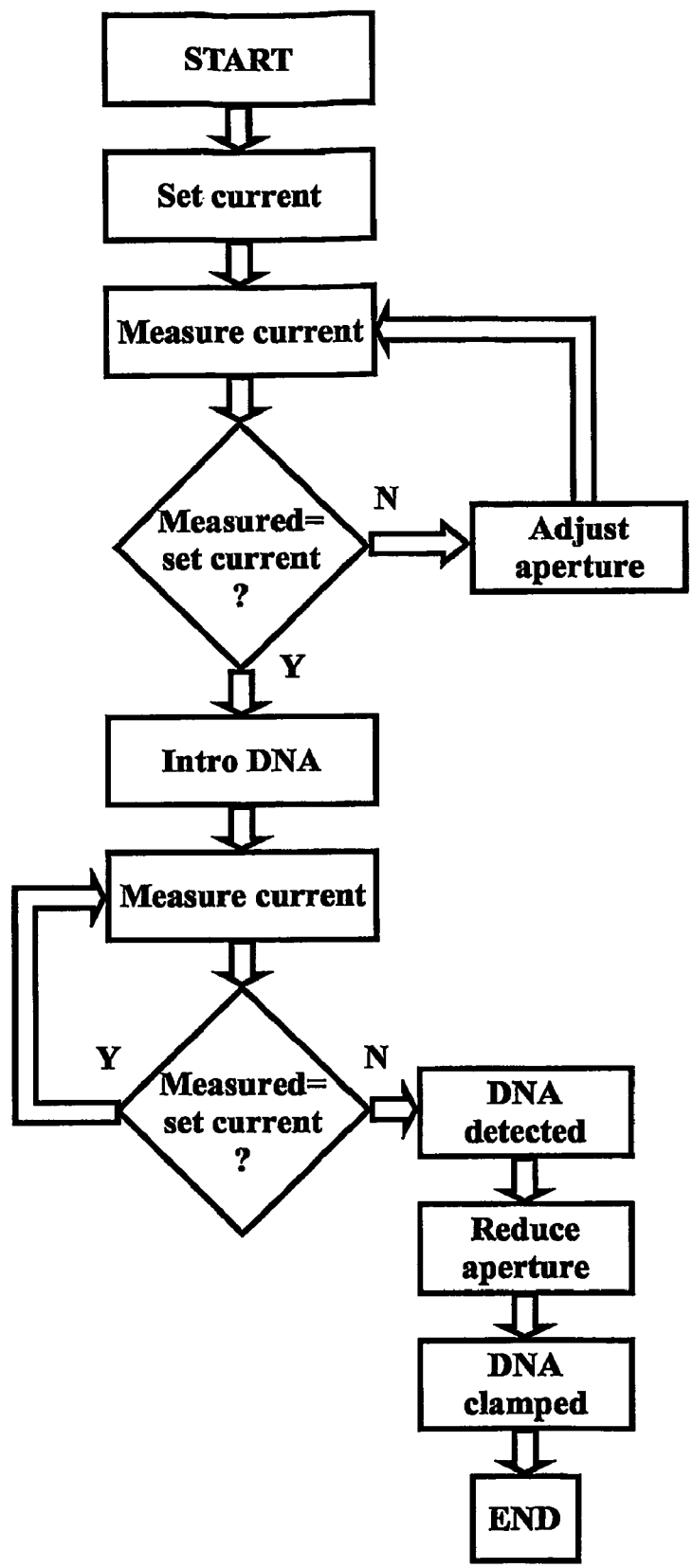
FIG. 9 is a flow chart depicting another possible mode of operation of the embodiment illustrated in FIG. 5.

FIG. 9 is a flow chart depicting another exemplary mode of operation of the device of the invention schematically illustrated in FIG. 8.

Figure 10:
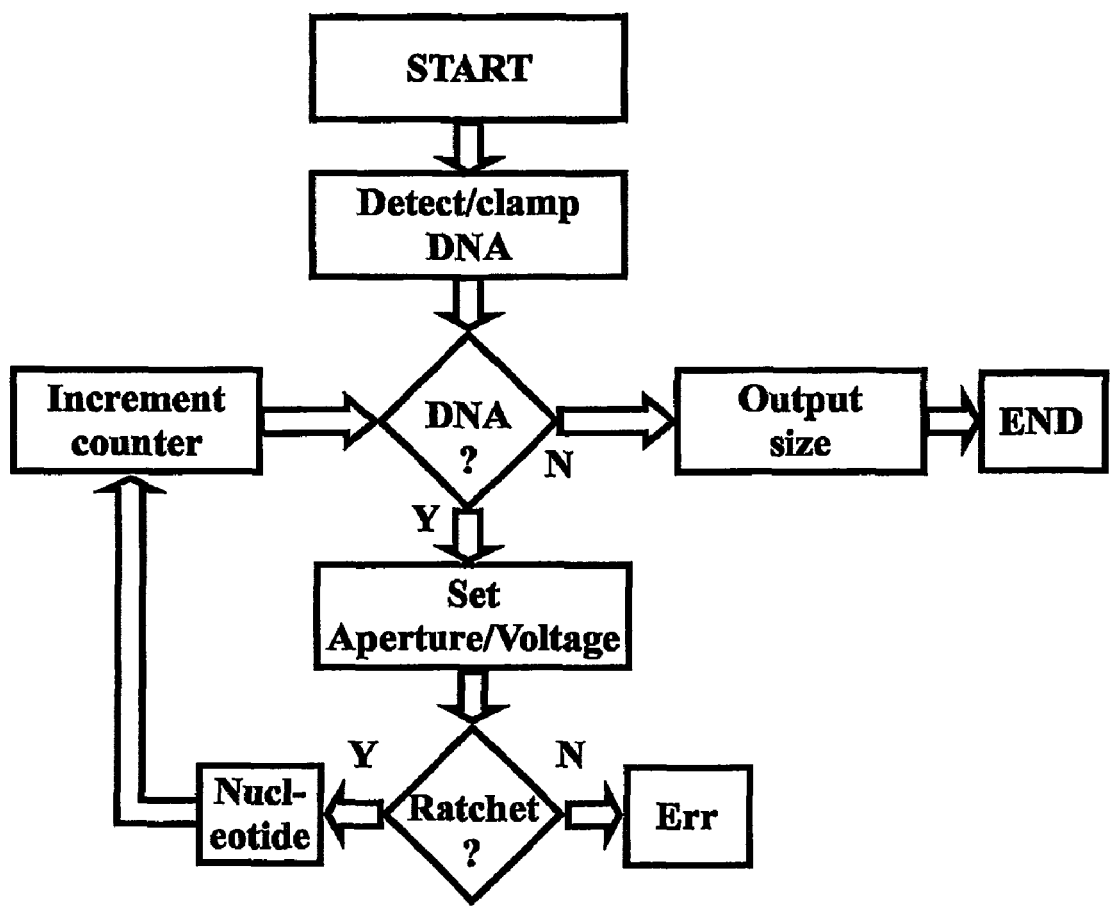
FIG. 10 is a flow chart depicting another possible mode of operation of the embodiment illustrated in FIG. 5.

FIG. 10 is a flow chart depicting another exemplary mode of operation of the device of the invention schematically illustrated in FIG. 8.

In this example, reference will be made to the application of this device for characterizing biological polymers such as: deoxyribose nucleic acids (DNA) and chemical modifications thereof; ribose nucleic acids (RNA) and chemical modifications thereof, although other polymers may also be characterized.

This example of the invention is particularly well suited to the characterization of individual polymer molecules, although it is equally well suited to the characterization of homogeneous preparations of heteropolymer molecules of the same length as well as heterogeneous mixtures of molecules, leading to a characterization of the polymer mixture for polymer length distribution, polymer copy number and polymer sequence structure.

With precise control of the ratcheting mechanism, the incremental shunting-clamping of the nucleic acid polymer can be tuned to specific molecular characteristics, such as the molecular volume, which differ for each of the four DNA monomer subunit residues.

With precise control of the ratcheting mechanism, the incremental shunting-clamping of the deoxyribose nucleic acid polymer can be tuned to gate monomeric subunit residues on the basis of molecular volume. Thus, the combined signals that facilitate the ratcheting of a DNA polymer through the deformable aperture can be set to incrementally ratchet the smallest monomer subunit (C), smallest two monomer subunits (C, T), smallest three monomer subunits (C, T, A), or all four monomer subunit (C, T, A, G).

Thus, for each monomer subunit in the DNA polymer chain, a cycle of incremental shunting through the progressively increasing deformable aperture until a successful ratcheting event has occurred win yield the identity of each DNA monomer subunit in a sequential stepwise fashion.

In another variation, the application of a pulse of prescribed width and duration sufficient to allow the voltage driven translocation of single-stranded nucleic acid polymer through the deformable aperture by only any one of the four single nucleic acid monomeric subunit residues coupled with sensitive single channel recording techniques can validate the presence of a single monomeric subunit and allow identification of the monomeric subunit on the basis of changes in the measured single channel recordings.

Sequential application of applied prescribed pulses of differing amplitude and/or duration would allow subsets of the of monomeric subunit residue to be identified and would lead to further characterization of the nucleic acid polymer on the basis of monomeric subunit residue sequence and length. It will also be appreciated that prescribed pulses could be configured to allow specific dinucleotide combinations to translocate the deformable aperture. It will also be appreciated that prescribed pulses could be configured to allow specific trinucleotide combinations to translocate the deformable aperture. It will also be appreciated that prescribed pulses could be configured to allow specific nucleotide motifs to translocate the deformable aperture.

Figure 11:
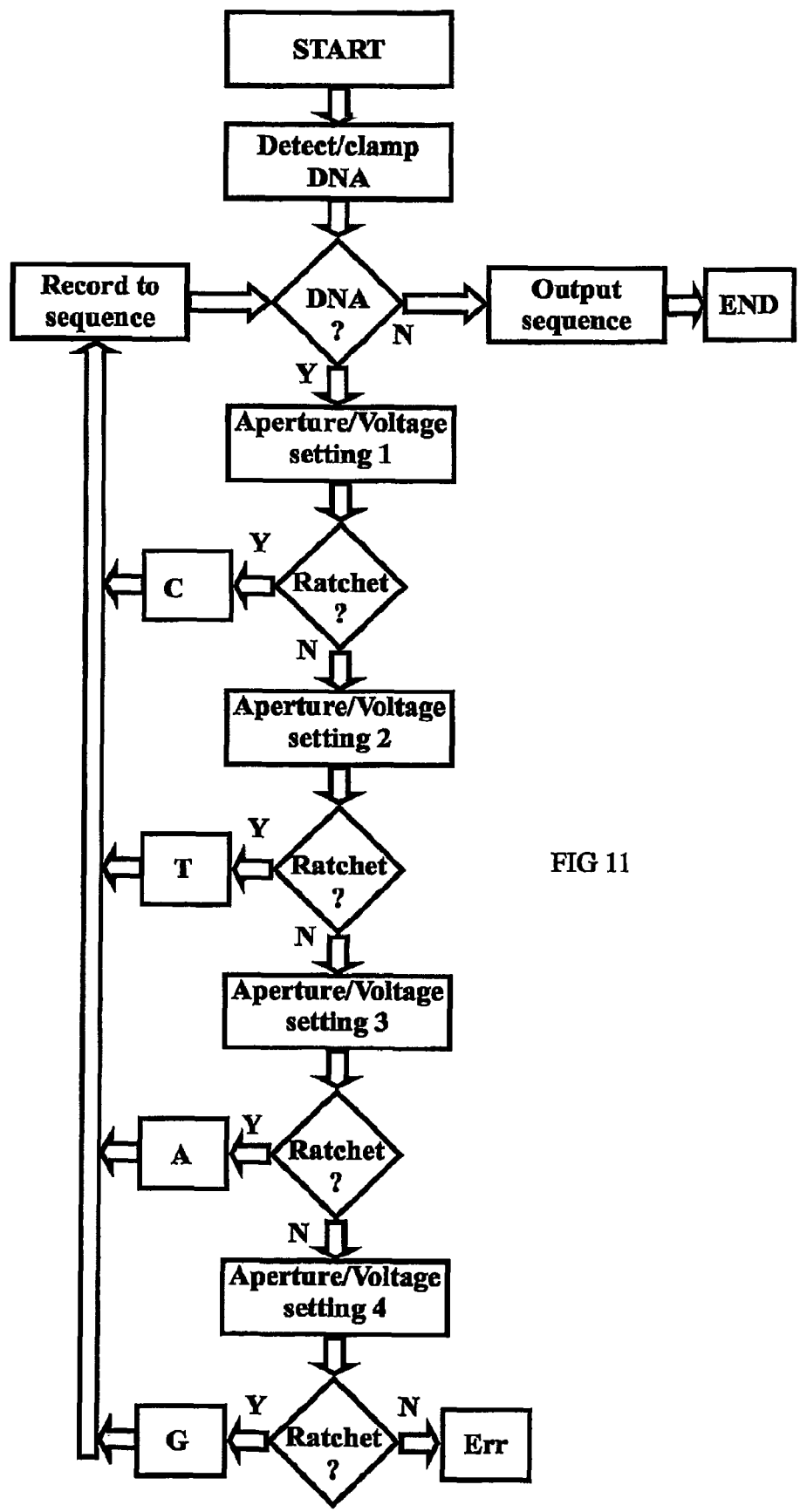
FIG. 11 is a flow chart depicting another possible mode of operation of the embodiment illustrated in FIG. 5 for determining the nucleotide sequence of DNA.

FIG. 11 is a flow chart depicting another exemplary mode of operation of the device of FIG. 5 for determining the nucleotide sequence of DNA.

In accordance with the above embodiments of the present invention it will be appreciated that other measurable parameters of the deformable material in which the deformable aperture is fabricated can be utilized including those selected from the group comprising, but not limited to: capacitance; resistance; conductivity; opacity; transparency; length; width; height; volume; thermal conductivity; dielectric properties; or measurable parameters linked to the actuation mechanism by which the at least one deformable aperture is adjusted, selected from the group comprising, but not limited to: capacitance; resistance; conductivity; stepper position; motor coil inductance; can be used as a means of monitoring changes in the size and/or geometry of the at least one deformable aperture. Variation in the state of these parameters as at least one occluding particle traverses the aperture can be used to detect and/or characterize and or control at least one occluding particle.

Figure 12:
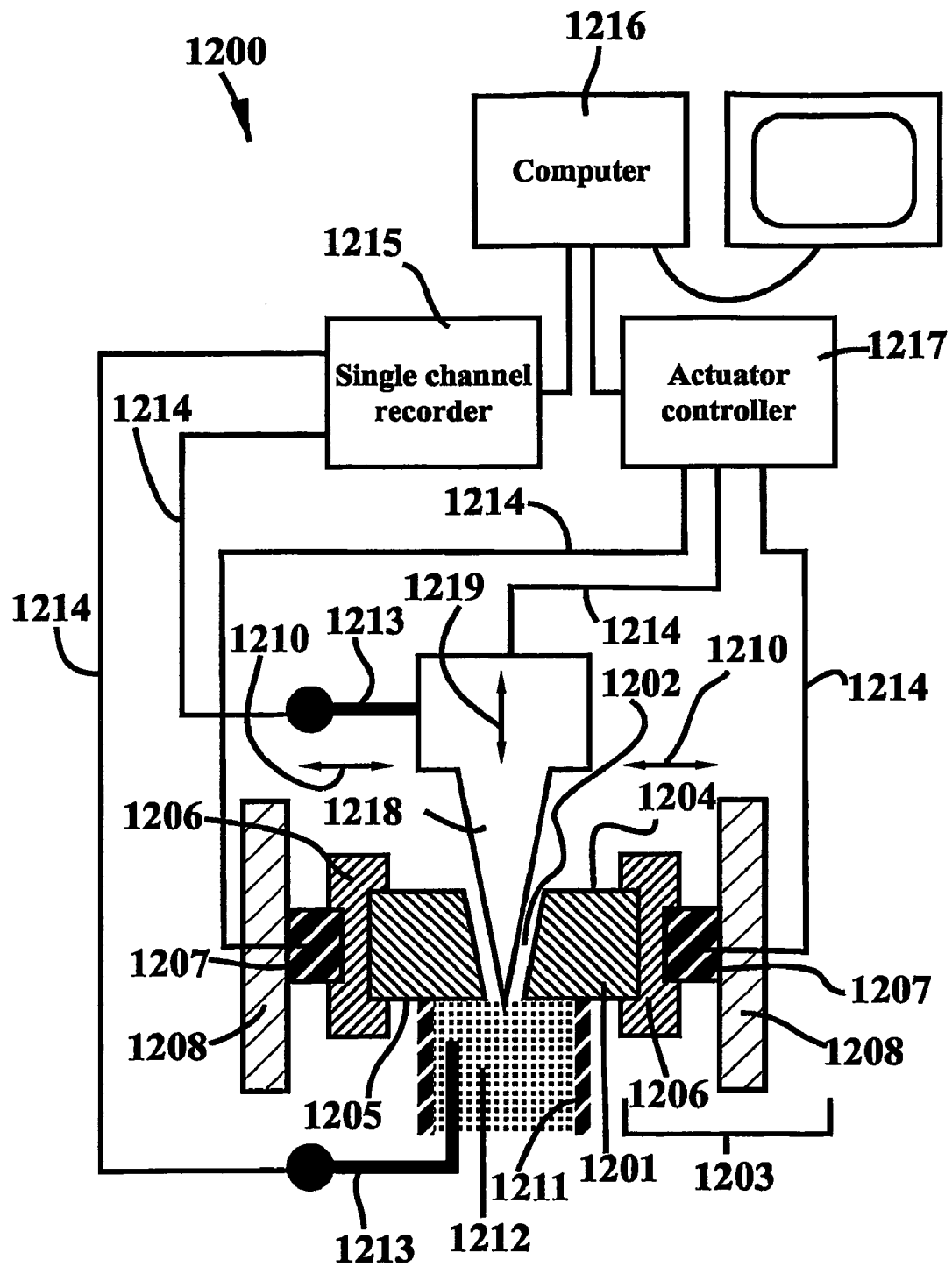
FIG. 12 schematically illustrates a possible possible for fabricating a deformable aperture in the preferred embodiment of the invention schematically illustrated in FIG. 5.

FIG. 12 is a simplified schematic illustration of an arrangement for fabricating at least one deformable aperture in a deformable material.

The deformable aperture is fabricated in a sheet of deformable material as already described. In one preferred example the deformable material is polyurethane. However, the deformable material can be any other material selected from the group comprising, but not limited to: natural and synthetic rubbers; natural polymers, proteins, polypeptides, polysaccharides; plastics; doped conducting plastics; hydrocarbon plastics; perfluorocarbon plastics; latex materials; thermoplastic deformable materials; thermoplastic polyurethane (ethers and esters) deformable materials; olefin-based deformable materials including polypropylene, polyethylene, cyclic olefins; styrene-based deformable materials; polyamide-based deformable materials; polyester-based deformable materials; nitryl-based deformable materials; ethylene chloride copolymer cross-linked alloys; silicone deformable materials; silicate, silicon, doped silicon, or other semiconductor based materials; metals, or metal alloys. The deformable aperture can also be made from a composite deformable material consisting of a combination of one or more such materials.

Furthermore, modifications to the deformable aperture can take the form of chemical modifications chemically or physically bonded to the surface of the deformable aperture to render it hydrophobic, super-hydrophobic, hydrophilic, or to have specific physico-chemical properties. Relevant examples include, but are not limited to, chemicals, silanes and silicones. Surface modifications can also take the form of physical modifications made to the deformable material of the aperture by surface patterning to render it hydrophobic, super-hydrophobic, hydrophilic, or to have specific physico-chemical properties or optical or magnetic or other physical properties.

One way of fabricating the deformable aperture is by penetrating a sheet of deformable material to form a vacancy in the deformable material through which a continuous path extends from one side of the sheet, through the deformable material to the opposing side of the sheet.

In FIG. 12 a device 1200 comprises a sheet of deformable material 1201 adapted to be mechanically deformed by a machine 1203. The deformable material 1201 has an upper surface 1204 and a lower surface 1205. The opposing edges of the deformable material 1201 are held firmly by clamps 1206. The clamps 1206 attach the deformable material 1201 to mechanical actuators 1207 mounted on the casing 1208 of the machine 1203. The mechanical actuators 1207 provide deformation adjustment of the deformable material 1201. The machine 1203 mechanically deforms the deformable material 1201 as indicated by the double-headed arrows 1210. The device includes a boundary 1211 for holding a volume of ionic fluid, preferably an aqueous solution of potassium chloride 1212, in which an electrode of silver chloride 1213 sits. An electrochemically etched tungsten metal probe 1218 is positioned above the deformable material 1201 complete with its own electromechanical actuators (not shown) capable of being positioned as indicated by the double-headed arrows 1219. The probe 1218 itself acts an electrode 1213. The electrodes 1213 are connected by electrical connectors 1214 to a single channel recording apparatus 1215 that is coupled via a programmable logic device 1216 to a mechanism for controlling the actuator 1217 for adjusting the size of the deformable material 1201 and the position of the probe 1218.

In operation to form a deformable aperture, the probe 1218 is caused first to be positioned on the surface 1204 of the deformable material 1201, and then to penetrate the surface of the deformable material 1204 and to extend through the deformable material 1201 and exit the opposing surface of the deformable material 1205. This sequence of operation is then followed by partial or complete withdrawal of the probe 1218 from the deformable material 1201, thereby creating at least one aperture 1202 in the deformable material 1201.

The device 1200 includes a mechanism for monitoring the size of the deformable aperture 1202 in which the probe 1218 functions as an electrode 1213 and the silver chloride electrode 1213 confers the ability to monitor the ionic current through the deformable aperture 1202 by electrical connectors 1214 connected to a single channel recording apparatus 1217. The recording apparatus 1217 is coupled via a programmable logic device 1216 to the mechanism for controlling the actuator for adjusting the penetration of the probe 1210 through the deformable material 1201.

The probe 1218 is positioned by actuators from the group comprising, but not limited to, mechanical actuators, electromagnetic actuators, electrostatic actuators and piezoelectric actuators. The probe may be prepared by grinding and polishing processes, molding processes, extrusion processes, electrochemical etching processes or lithographic processes. The probe may be of a type having a sharp point or a cutting tool with a defined shape or a scanning probe microscopy probe or a scanning tunneling microscopy probe or an atomic force microscopy probe. The probe can be heated or cooled with respect to the deformable material and can be pushed through the deformable material, thereby cutting or separating or melting the fabric of the deformable material, or rotated or moved so as to drill out or otherwise create the aperture in the deformable material.

The extent of the deformable material penetration by the probe 1218 may be determined by measurement of the electrical current or electrical tunneling current through the deformable aperture 1202 between the probe 1218 and an electrically conducting medium of ionic solution 1212 on the opposing side 1205 of the deformable material 1201 to the side 1204 on which the probe entered the deformable material 1201. Preferably, the adjustment mechanism is coupled to the mechanism for monitoring the size of the deformable aperture to create a feedback loop to control the size of the deformable aperture in which the feedback loop is selected from the group comprising, but not limited to, analog feedback loops, electronic feedback loops and computer controlled feedback loops.

The monitoring of the ion current flux through the aperture by single channel recording techniques is an inexpensive, viable method that has been used widely since the invention of the Coulter counter. Modern single channel recording instruments are sensitive enough to detect and record the movements of single ions taking place in the range of a few microseconds to milliseconds and comprise single channel recording instrumentation which can apply a variable range of voltages from about +1000 millivolts to about −1000 millivolts across the deformable material containing the aperture, a very low-noise current amplifier and current injector and analog to digital converters (ADCs) that can be interfaced to digital electronic computers using data acquisition software and electronic storage media (e.g. computer disk, magnetic tape). Equipment meeting these criteria is readily available, such as from Axon Instruments, Union City, Calif. USA (e.g. Axopatch 200B systems; pClamp 9.0 software).

In the present example, a feedback loop is established for controlling the size of the deformable aperture by utilizing the recording apparatus 1215, a programmable logic device 1216 and the actuator controller mechanism 1217. The adjustment mechanism for adjusting the penetration of the probe 1218 is computer controllable, thus allowing for the degree of penetration to be prescribed by algorithms.

The adjustment mechanism comprise the clamps 1206 attaching the deformable material 1201 to the actuators 1207 mounted on the casing 1208 for adjusting the deformable material 1201 and the adjustment mechanism (not shown) of the probe 1218 are electronically coupled to the mechanism for monitoring the conductance of the deformable material 1201 prior to, during and post the formation of the deformable aperture 1202.

Figure 13:
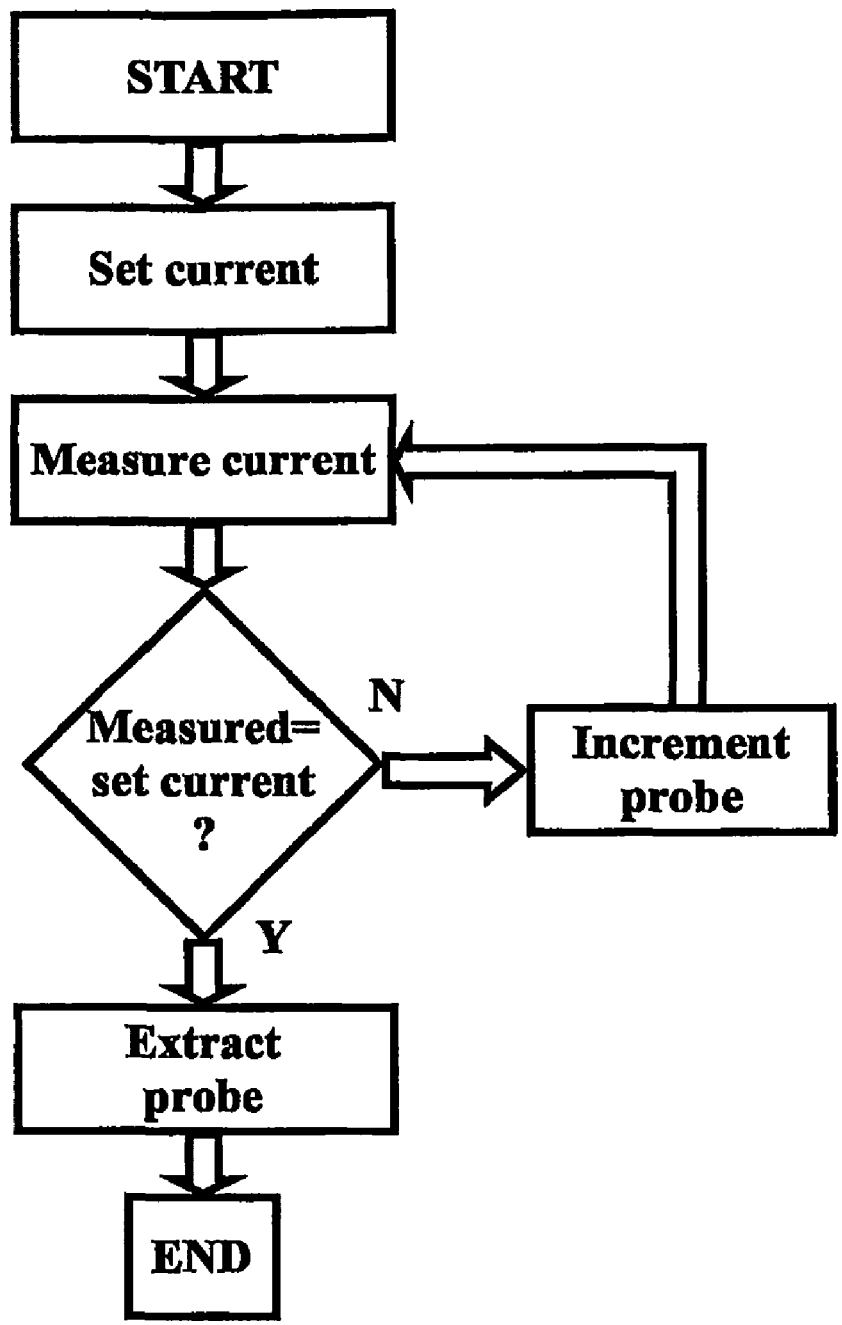
FIG. 13 shows a flow chart depicting a possible mode of operation of the possible schematically illustrated in FIG. 12.

FIG. 13 is a flow chart depicting one exemplary mode of operation of the device of FIG. 12 for fabricating the deformable aperture in the sheet of deformable material.

The deformable material may be deformed prior to or during, or post the formation of the aperture.

The deformable material may be deformed by mechanical deformation of the deformable material by a method selected from the group comprising, but not limited to, applying tension or compression or torsion or twisting or flexing, or applying strain to the deformable material.

Furthermore the deformable material may be deformed by heating or cooling of the deformable material.

Furthermore the penetration of the deformable material may be by one or more probes operated simultaneously or sequentially.

Furthermore the deformable aperture may formed in the deformable material by penetration of the deformable material by a beam of particles, or a beam of electromagnetic radiation, directed onto the surface of the deformable material and being caused to penetrate the surface of the deformable material and extend through the deformable material so as to exit from the opposing surface of the deformable material The beam of particles may include particles selected from the group comprising, but not limited to, atoms, atomic nuclei, electrons, ions, molecules and radioactive decay products. The beam of electromagnetic radiation may include electromagnetic radiation selected from the group comprising, but not limited to, photons, coherent light and laser light.

The beam of particles or electromagnetic radiation may include beams of particles or electromagnetic radiation focused by optical, magnetic or electromagnetic lenses and physical windows, and the size of the aperture may be monitored by measuring the particle beam flux through the aperture with a suitable particle counter placed on the side of the deformable material opposite to the particle beam source. Preferably the means for controlling the beam of particles or electromagnetic radiation is coupled to the mechanism for monitoring the size of the deformable aperture to create a feedback loop for controlling the size of the deformable aperture, the feedback loop being selected from the group comprising, but not limited to, analog feed back loops, electronic feedback loops and computer controlled feedback loops.

Alternatively the deformable aperture may be formed by penetration of the deformable material by at least one ballistic particle directed onto the surface of the deformable material and caused to penetrate the surface of the deformable material and extend through the deformable material before exiting the opposing surface of the deformable material.

Furthermore the deformable aperture may formed or modified by electrochemical etching of the deformable material.

Furthermore the deformable aperture may formed in the deformable material by mechanically fracturing the deformable material. In one example the deformable material is cooled to a solid non-deformable material and then fractured. Furthermore the deformable aperture may formed in the deformable material during the fabrication of the deformable material which includes, but is not limited to, one or more processes such as fabrication by polymerization, by molding, by casting, by injection molding, by compression molding, by vacuum evaporation, by electrochemical deposition, by formation at an interface and by embossing of the deformable material.

It is common that, when samples of heterogeneous particle size distribution are analyzed using apertures, blockages can occur in apertures, requiring that the blockages become dislodged for further use of the aperture. It is thus advantageous make provision for clearing of the deformable aperture of blockages by adjustment of the deformable aperture to dislodge the blockage. This can be done by detecting the presence of the blockage and then adjusting the size and/or geometry of the deformable aperture, and optionally adjusting the size and polarity of the ionic current through the deformable aperture, to dislodge the blockage.

The above described embodiments of the invention have a number of important advantages: they are easily fabricated from inexpensive materials reducing costs; the deformable apertures can be tuned to the appropriate geometry post fabrication; the ability to adjust the aperture geometry renders it capable of discriminating a plurality of differently sized particles; and by adjusting the geometry it is capable of dislodging blockages, thus alleviating the need for frequent and costly apparatus dismantlement. Furthermore the above described embodiments offer new modes of operation, and are particularly well suited to miniaturization. Other advantages will be apparent from reading this specification.

Deformable apertures as described above are anticipated to find utility in a plurality of applications including detecting, measuring and controlling of particles and/or detecting, measuring and controlling of electromagnetic radiation.

The invention claimed is:

1. A particle-sensitive device incorporating deformable elastomeric material containing a deformable aperture providing a path for particles, adjustment means for deforming the deformable aperture by deforming the elastomeric material to change at least one of the parameters of the path provided by the deformable aperture, and monitoring means for monitoring at least one of the parameters of the path provided by the deformable aperture and providing feedback indicative of the monitored parameter to the adjustment means, wherein the device is particle-sensitive, and wherein the deformable elastomeric material is provided as a sheet, the sheet being perforated to provide the deformable aperture.

2. A device according to claim 1, wherein the adjustment means is adapted to change the geometry and/or size of the deformable aperture to increase and/or to reduce the diameter and/or path length of the deformable aperture.

3. A device according to claim 1, wherein the deformable aperture has a cross-sectional area of less than 3 mm$^2$.

4. A device according to claim 1, wherein the monitoring means is configured to count particles which pass through the aperture.

5. A device according to claim 1, wherein the monitoring means is configured to characterize a structure of a particle.

6. A device according to claim 1, configured such that the deformable aperture clamps a particle by closure of the deformable aperture on the particle.

7. A particle-sensitive device incorporating deformable elastomeric material containing a deformable aperture providing a path for particles, adjustment means for deforming the deformable aperture by deforming the elastomeric material to change at least one of the parameters of the path provided by the deformable aperture, and monitoring means for monitoring at least one of the parameters of the path provided by the deformable aperture and providing feedback indicative of the monitored parameter to the adjustment means, wherein the device is particle-sensitive, wherein the deformable elastomeric material is provided as a sheet, and wherein the adjustment means is arranged to cause deformation of the sheet in one or more directions parallel to a plane of the sheet.

8. A device according to claim 7, wherein the adjustment means is adapted to change the geometry and/or size of the deformable aperture to increase and/or to reduce the diameter and/or path length of the deformable aperture.

9. A device according to claim 7, wherein the deformable aperture has a cross-sectional area of less than 3 mm$^2$.

10. A device according to claim 7, wherein the monitoring means is configured to count particles which pass through the aperture.

11. A device according to claim 7, wherein the monitoring means is configured to characterize a structure of a particle.

12. A device according to claim 7, configured such that the deformable aperture clamps a particle by closure of the deformable aperture on the particle.

13. A particle-sensitive device incorporating deformable elastomeric material containing a deformable aperture providing a path for particles, adjustment means for deforming the deformable aperture by deforming the elastomeric material to change at least one of the parameters of the path provided by the deformable aperture, and monitoring means for monitoring at least one of the parameters of the path provided by the deformable aperture and providing feedback indicative of the monitored parameter to the adjustment means, wherein the device is particle-sensitive, wherein the deformable elastomeric material is provided as a sheet having two main surfaces, and wherein the path for particles extends through the sheet from one of said surfaces to the other of said surfaces.

14. A device according to claim 13, wherein the adjustment means is adapted to change the geometry and/or size of the deformable aperture to increase and/or to reduce the diameter and/or path length of the deformable aperture.

15. A device according to claim 13, wherein the deformable aperture has a cross-sectional area of less than 3 mm$^2$.

16. A device according to claim 13, wherein the monitoring means is configured to count particles which pass through the aperture.

17. A device according to claim 13, wherein the monitoring means is configured to characterize a structure of a particle.

18. A device according to claim 13, configured such that the deformable aperture clamps a particle by closure of the deformable aperture on the particle.

* * * * *